United States Patent
Fang et al.

(10) Patent No.: US 7,723,324 B2
(45) Date of Patent: May 25, 2010

(54) IMIDAZO[1,2-A]PYRIDINE ANXIOLYTICS

(75) Inventors: Q. Kevin Fang, Wellesley, MA (US);
Paul Grover, Plainville, MA (US);
Thomas P. Jerussi, Charleston, SC (US)

(73) Assignee: Sepracor, Inc., Marlborough, MA (US)

( * ) Notice: Subject to any disclaimer, the term of this patent is extended or adjusted under 35 U.S.C. 154(b) by 424 days.

(21) Appl. No.: 10/595,592

(22) PCT Filed: Oct. 28, 2004

(86) PCT No.: PCT/US2004/035822

§ 371 (c)(1),
(2), (4) Date: Jul. 3, 2007

(87) PCT Pub. No.: WO2005/044818

PCT Pub. Date: May 19, 2005

(65) Prior Publication Data

US 2008/0096867 A1   Apr. 24, 2008

Related U.S. Application Data

(60) Provisional application No. 60/515,043, filed on Oct. 28, 2003.

(51) Int. Cl.
| | |
|---|---|
| A61K 31/437 | (2006.01) |
| A61K 31/454 | (2006.01) |
| A61K 31/55 | (2006.01) |
| A61P 25/00 | (2006.01) |
| A61P 25/04 | (2006.01) |
| A61P 27/02 | (2006.01) |
| C07D 211/40 | (2006.01) |
| C07D 401/14 | (2006.01) |
| C07D 471/04 | (2006.01) |

(52) U.S. Cl. .............. 514/212.08; 514/300; 514/322; 546/121; 546/199; 540/524

(58) Field of Classification Search .............. 546/121, 546/199; 514/300, 212.08, 322; 540/524
See application file for complete search history.

(56) References Cited

U.S. PATENT DOCUMENTS

| 4,382,938 A | 5/1983 | Kaplan et al. |
| 4,501,745 A | 2/1985 | Kaplan et al. |
| 4,650,796 A * | 3/1987 | George et al. .......... 514/212.08 |
| 4,713,381 A | 12/1987 | Ao et al. |

FOREIGN PATENT DOCUMENTS

| EP | 0092458 | 10/1983 |
| FR | 2647451 | * 11/1990 |
| SU | 522187 | * 9/1976 |
| WO | 02/066477 | 8/2002 |
| WO | 02/066478 | 8/2002 |
| WO | 02066477 | * 8/2002 |
| WO | 02066478 | * 8/2002 |
| WO | 03/000682 | 1/2003 |
| WO | 03/097062 | 11/2003 |

OTHER PUBLICATIONS

Moutou et al., Heterocycles (1997), 45(5), 897-910.*
Van Hulten et al., Pharmacoepidemiology and drug safety, (Aug. 1999), vol. 8, No. 5, pp. 325-330.*

(Continued)

*Primary Examiner*—D. Margaret Seaman
*Assistant Examiner*—Niloofar Rahmani
(74) *Attorney, Agent, or Firm*—Heslin Rothenberg Farley & Mesiti P.C.

(57) ABSTRACT

Imidazo[1,2-a]pyridines of the formulae I and II:

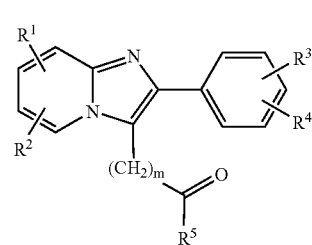

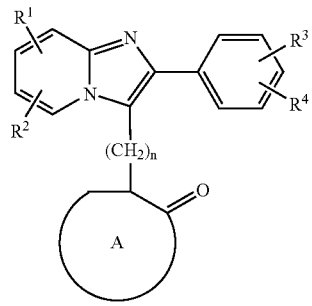

are disclosed. The compounds are useful to treat anxiety and insomnia. Pharmaceutical compositions and methods are also disclosed. A representative compound of the invention is:

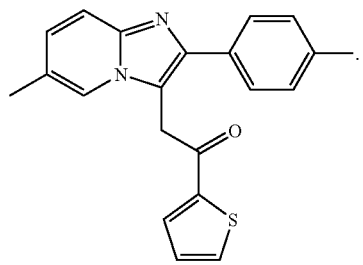

10 Claims, 3 Drawing Sheets

OTHER PUBLICATIONS

P. George et al., "Imidazopyridines: Towards Novel Hypnotic and Anxiolytic Drugs," Il Farmaco, 46(1), 277-288 (1991).

S. P. Gupta et al., "Quantitative Structure-Activity Relationship Studies on some Nonbenzodiazepine Series of Compunds acting at the Benzodiazepin Receptor," Bioorg. Med. Chem., 6, 2213-2218 (1998).

De Clerck, Isabel; Daenens, P., "Development of a radioimmunoassay for the determination of zolpidem in biological samples," Analyst (Cambridge, United Kingdom) 122(10), 1119-1124 (1997).

Communication from the European Patent Office for European Counterpart Application No. 04 796 657.7-2103 dated Apr. 28, 2008.

Office Action for U.S. Appl. No. 11/532,402 dated Oct. 8, 2008.

Colletti et al.: Journal of Medicinal Chemistry, 46(3), pp. 349-352 (2003).

Joughin et al.: British Journal of Addiction, 86, pp. 449-455 (1991).

* cited by examiner

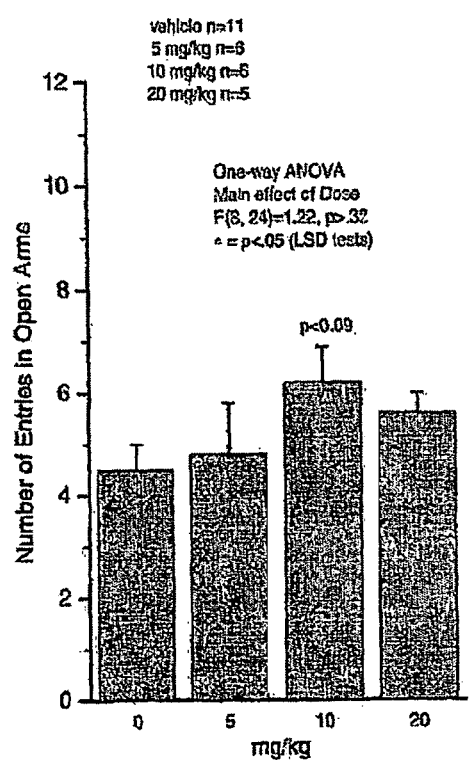
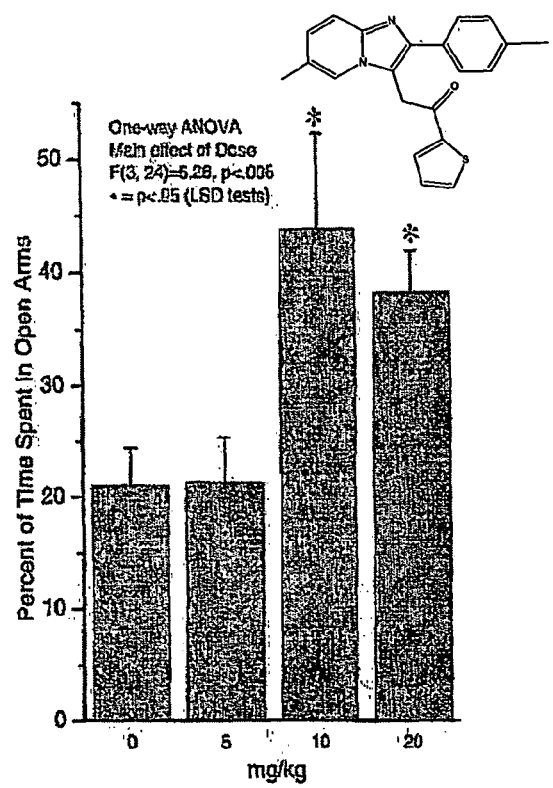
Figure 1a                    Figure 1b

IMIDAZO[1,2-A]PYRIDINE ANXIOLYTICS

CROSS REFERENCE TO RELATED APPLICATIONS

This application is a 371 filing of PCT International application no. PCT/US04/35822 filed on Apr. 28, 2006 which claims the priority of U.S. Application No. 60/515,043 filed on Oct. 28, 2003 and U.S. Application 2004/035822 filed on Oct. 28, 2004. The disclosures of these applications and all other patents, published applications, and other references cited therein are hereby incorporated by reference in their entirety.

FIELD OF THE INVENTION

The invention relates to imidazo[1,2-a]pyridines useful in the treatment of anxiety and insomnia.

BACKGROUND OF THE INVENTION

Gamma-aminobutyric acid (GABA) is the major inhibitory neurotransmitter within the central nervous system (CNS). $GABA_A$ receptors are ligand gated ion channels that are made up from a large range of different subunits ($\alpha$1-6, $\beta$1-3, $\gamma$1-3, $\delta$, $\epsilon$, $\pi$, and $\theta$). Each receptor complex comprises five subunits, with the dominant in vivo combination thought to be $2\alpha2\beta1\gamma$. Several therapeutic agents exert their effects by modulating this receptor complex, but adverse effects, particularly sedation, are common and, in part, a consequence of poor subunit selectivity. The existence of a large number of different GABA-A receptors resulting from subunit heterogeneity indicates that there are excellent prospects for developing more selective drugs for the treatment of CNS disorders with reduced side effects. To date, the majority of the ligands that have been identified bind to $\alpha$ subunits that are sensitive to classical benzodiazepines, namely $\alpha$1, $\alpha$2, $\alpha$3 and $\alpha$5. Without exception, these ligands bind allosterically to the receptor, rather than by occupying the orthosteric (GABA) site and can exert a range of pharmacological activities including agonists, antagonists, partial agonists, and inverse agonists.

Agents that bind or interact with the modulatory sites on the $GABA_A$ receptor complex, such as, the benzodiazepine receptor, can have either enhancing effect on the action of GABA, i.e. a positive modulatory effect of the receptor (agonists, partial agonists), an attenuating effect on the action of GABA, i.e. negative modulation of the receptor (inverse agonists, partial inverse agonists), or they can block the effect of both agonists and inverse agonists by competitive block (antagonists or ligands without intrinsic activity).

The binding of the compounds of the current invention at or near the benzodiazepine receptor complex suggests that the compounds of the invention may facilitate the inhibitory action of the neurotransmitter GABA and therefore its synaptic effects. As stated above, benzodiazepine receptors, which can be located both within the central nervous system and peripherally (e.g., in the endocrine system), are comprised of macromolecular complexes characterized by sites for binding of the benzodiazepines and GABA. The benzodiazepine receptor complex is further associated with, and interacts with, a transmembrane channel for chloride ion transport. The effect of the compounds of the current inventions' interaction with the benzodiazepine receptor/GABA receptor/chloride channel complex is to cause GABA to inhibit cerebral neuronal discharge, presumably by increasing membrane conductance of chloride ion, thus stabilizing membrane potentials and dampening excitatory input. (See Meldrum, B. S. Brit. J. Clin. Pharm. 27 (suppl. 1), 3S-11S (1989)). Through mediation of this process, the compounds of the current invention may be useful in treating anxiety disorders and a number of other conditions in which GABA is believed to exert a physiologic role. These conditions include psychiatric disorders, convulsive disorders, aggressive behavior, muscle spasms or tensing, depressive or bipolar disorders, cognitive disorders, sleeping disorders, neurodegenerative eye diseases, neurodegeneration, pain, emesis, or eating disorders. The present invention also includes methods for treating the above-described conditions or disorders in a human by administering the compounds of the invention to the human.

Agonists generally produce muscle relaxant, hypnotic, sedative, anxiolytic, and/or anticonvulsant effects, while inverse agonists produce proconvulsant, antiinebriant, and anxiogenic effects. Compounds with anxiolytic effects, but without or with reduced muscle relaxant, hypnotic and sedative effects are characterized as partial agonists. Partial inverse agonists are considered to be useful as cognition enhancers.

SUMMARY OF THE INVENTION

In one aspect the invention relates to imidazo[1,2-a]pyridines of the formulae I and II:

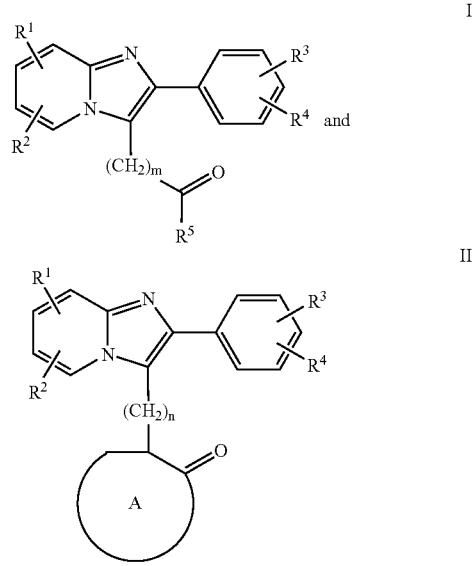

In these compounds $R^1$, $R^2$, $R^3$ and $R^4$ are chosen independently from hydrogen, halogen, loweralkyl, loweralkoxy, hydroxy, dialkylamino, cyano, acyl, perfluoroloweralkyl and loweralkylsulfonamido. $R^5$ is chosen from $C_1$ to $C_{20}$ hydrocarbon, substituted aryl, heterocyclyl and substituted heterocyclyl, with the proviso that if $R^5$ is a nitrogen heterocycle, the nitrogen cannot be the point of attachment. A is chosen from a carbocycle, a hetero cycle, a substituted carbo cycle and a substituted heterocycle. m is one, two or three; and n is zero, one or two.

In another aspect the invention relates to pharmaceutical compositions comprising a pharmaceutically acceptable carrier and a compound of formula I or II, or a salt thereof.

In another aspect the invention relates to a method for treating anxiety disorders, psychiatric disorders, convulsive disorders, aggressive behavior, muscle spasms or tension, depressive or bipolar disorders, cognitive disorders, sleeping disorders, neurodegenerative eye diseases, neurodegeneration, pain, emesis, or eating disorders comprising administering to a patient a therapeutically effective amount of a compound of formula I or II.

In yet another aspect, the invention includes a method for inhibiting a benzodiazepine receptor comprising administering to a patient a therapeutically effective amount of a compound of formula I or II.

BRIEF DESCRIPTION OF THE DRAWINGS

FIGS. 1a, 2a, and 3a are graphs showing the results of in vivo testing of various compounds of the present invention, as indicated by the Number of Entries in Open Arms vs. mg/kg (dose of administered compound); and FIGS. 1b, 2b, and 3b are graphs showing the results of in vivo testing of various compounds of the present invention, as indicated by the Number of Entries in Open Arms vs. mg/kg (dose of administered compound).

DETAILED DESCRIPTION OF THE INVENTION

Figure 2A:
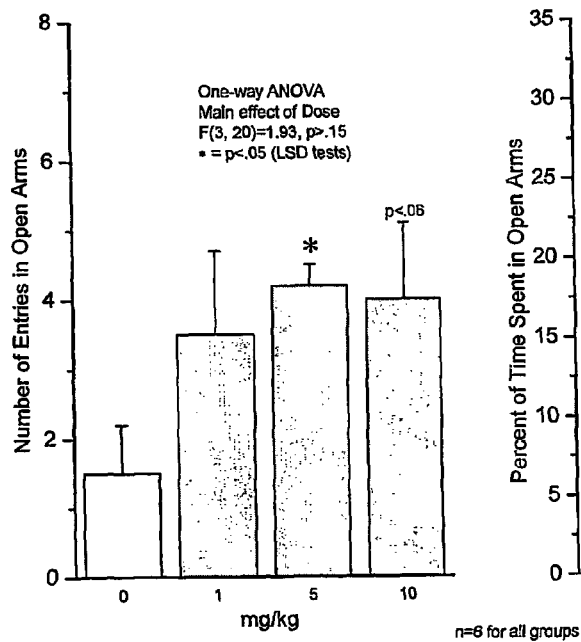

Compounds of the current invention are useful in treating anxiety disorders, which can have its etiology in both psychologic and physiologic factors. Emotional stress can precipitate anxiety neurosis which represents the individual's fear of losing control of such emotional drives as aggressive or dependency needs, and losing control of his resulting actions. Physiologically, anxiety is associated with autonomic nervous system discharge and the related neurohumoral processes. In acute anxiety attacks, lasting from a few minutes to an hour, the individual experiences a subjective sense of terror, for no evident reason, and perhaps a haunting dread of catastrophe. Chronic anxiety displays less intense symptoms of longer duration, characterized by uneasiness, nervousness, nagging uncertainty about future events, headache, fatigue, and subacute autonomic symptoms.

Furthermore, the compounds of the current invention are useful in treating psychotic disorders, which tend towards chronicity, which impair functioning, and which are characterized by psychotic symptoms of disturbed thinking, feeding, and general behavior. Clear, goal-directed behavior becomes difficult, while blunting and inappropriate affect are the most characteristic emotional changes. Auditory hallucinations can be common, and delusions of persecution are frequent, as are threats of violence, minor aggressive outbursts and aggressive behavior. Disturbances of movement can range from significant overactivity and excitement to retardation and stupor. Treatment has often included tranquilizers with the pharmacologic profile of compounds of the current invention, and other antipsychotic drugs, either orally or by long-acting depot injection to offset problems of patient compliance.

In addition, compounds of the invention are useful for treating other disorders such as convulsive disorders like epilepsy. Seizure disorders or epilepsy represent a broad group of central nervous system disorders of function that are characterized by recurrent, sudden, often brief attacks, which may alter consciousness, motor activity, sensory phenomena, and autonomic responses, and which may prompt inappropriate behavior. Recurrent seizure patterns of either an idiopathic or symptomatic etiology are terms epilepsy. The most common form of these recurrent but transient episodes are convulsive seizures, which may include loss of consciousness, motor function and control, and which may produce tonic or clonic jerking of the extremities. Pharmacological treatment of epilepsy has been directed to control based on seizure type, rather than etiology. Accordingly, the convulsions have been grouped in broad, but rather distinct types, including Tonic-clonic (Grand Mal), Partial (Focal) seizures, psychomotor (Complex partial) seizures, pyknoepileptic or Absence (Petit Mal) and the less frequent Myoclonic seizures.

The compounds of the current invention are also useful in the treatment of spasticity and acute muscle spasm. Spasticity represents not a single disorder, but rather a range of abnormalities of regulation of skeletal muscle that result from problems at various levels of the central nervous system. A predominant component is heightened muscle tone or hyperexcitability of tonic stretch muscle reflexes. While the pathopysiology of these disorders remains rather poorly understood, it often includes dysfunction of the descending spinal pathways. Presynaptic inhibition of motomeurons, as may be induced by GABA, or agents that in some respects resemble and/or exhibit the pharmacology of GABA provides some antispastic affect. Additionally, benzodiazepines, or drugs like compounds of the present invention that bind to the benzodiazepine receptor, may enhance the efficiency of inhibitory GABA-ergic transmission, and thus may provide some efficacy in the treatment or conditions of spasticity, particularly those due to spinal cord lesions. Acute muscle spasm may be associated with a variety of conditions including trauma, inflammation, anxiety, and pain.

The compounds of the current invention are useful for the treatment of sleep disorders. Difficulties in falling asleep, remaining asleep, sleeping for adequate lengths of time, or abnormal sleep behavior are common symptoms for those suffering with a sleep disorder. A number of sleep disorders, e.g., insomnia or sleep apnea, are described in the online *Merck Manual of Medical Information*. Insomnia is characterized by difficulty in sleeping or disturbed sleep patterns. Insomnia may be of a primary nature with little apparent relationship to intermediate somatic or psychic events, or secondary to some acquired pain, anxiety, or depression. Where possible, treatment is directed to the underlying cause of the condition; hypnotic medication is generally reserved for insomnia of emotional disturbances and for refractory cases due to more common causes.

Imidazo[1,2-a]pyridines of the formulae I and II:

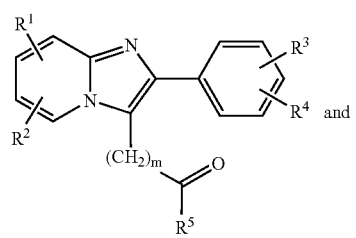

I

-continued

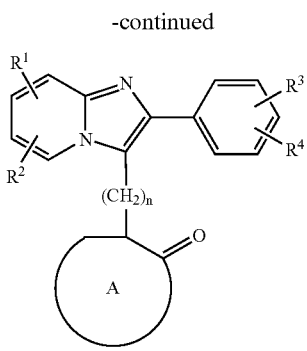

II exhibit affinity for the benzodiazepine receptor.

DEFINITIONS

Throughout this specification the terms and substituents retain their definitions.

Alkyl is intended to include linear, branched, or cyclic hydrocarbon structures and combinations thereof. Loweralkyl refers to alkyl groups of from 1 to 6 carbon atoms. Examples of lower alkyl groups include methyl, ethyl, propyl, isopropyl, butyl, s- and t-butyl and the like. Preferred alkyl groups are those of $C_{20}$ or below. Cycloalkyl is a subset of alkyl and includes cyclic hydrocarbon groups of from 3 to 8 carbon atoms. Examples of cycloalkyl groups include c-propyl, c-butyl, c-pentyl, norbornyl and the like.

$C_1$ to $C_{20}$ hydrocarbon includes alkyl, cycloalkyl, alkenyl, alkynyl, aryl and combinations thereof. Examples include phenethyl, cyclohexylmethyl, norbornyl and naphthylethyl.

Alkoxy or alkoxyl refers to groups of from 1 to 8 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Loweralkoxy refers to groups containing one to four carbons.

Acyl refers to groups of from 1 to 8 carbon atoms of a straight, branched, cyclic configuration, saturated, unsaturated and aromatic and combinations thereof, attached to the parent structure through an carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to four carbons.

Aryl and heteroaryl refer to a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or a tricyclic 13- or 14-membered aromatic or heteroaromatic ring system containing 0-3 heteroatoms selected from O, N, or S. The aromatic 6- to 14-membered carbocyclic rings include, e.g., benzene, naphthalene, indane, tetralin, and fluorene and the 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Heterocycle means a cycloalkyl or aryl residue in which from one to three carbons is replaced by a heteroatom selected from the group consisting of N, O and S. The nitrogen and sulfur heteroatoms may optionally be oxidized, and the nitrogen heteroatom may optionally be quaternized. Examples of heterocycles that fall within the scope of the invention include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, dioxane, tetrahydrofuran and the like. It is to be noted that heteroaryl is a subset of heterocycle in which the heterocycle is aromatic. Examples of heterocyclyl residues additionally include piperazinyl, 2-oxopiperazinyl, 2-oxopiperidinyl, 2-oxo-pyrrolidinyl, 2-oxoazepinyl, azepinyl, 4-piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl, benzothienyl, thiamorpholinyl, thiamorpholinylsulfoxide, thiamorpholinylsulfone, oxadiazolyl, triazolyl and tetrahydroquinolinyl.

Carbocycle is the complement of heterocycle. Carbocycle means a cycloalkyl or aryl residue in which all of the ring elements are carbon. It includes polycyclic and fused residues. Examples include cyclohexane, benzene, cyclopentadiene, naphthalene, phenanthrene, fluorene, norbornane, bicycloheptadiene, indane and bicyclooctane.

Substituted alkyl, aryl, cycloalkyl, heterocyclyl etc. refer to alkyl, aryl, cycloalkyl, or heterocyclyl wherein up to three H atoms in each residue are replaced with halogen, haloalkyl, hydroxy, loweralkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy.

The term "halogen" means fluorine, chlorine, bromine or iodine.

The term "perfluoroloweralkyl" refers to a lower alkyl fluorocarbon in which the hydrogen directly attached to the carbon atoms is completely replaced by fluorine.

The term "loweralkylsulfonamido" refers to a residue of formula (lower alkyl-$SO_2$NR—), wherein R is hydrogen or a $C_1$ to $C_{20}$ hydrocarbon, and wherein the point of attachment is through N.

It will be understood that "substitution", "substituted" or "substituted with" includes the implicit proviso that such substitution is in accordance with permitted valence of the substituted atom and the substituent, and that the substitution results in a stable compound, e.g., which does not spontaneously undergo transformation such as by rearrangement, cyclization, elimination, etc.

The term "method of treating anxiety disorders" as used herein means relief from the symptoms or the prevention of anxiety disorders, which include, but are not limited to, panic disorder with or without agoraphobia, agoraphobia without history of panic disorder, animal or other phobias including social phobias, obsessive-compulsive disorder, stress disorders including post-traumatic and acute stress disorder, situational anxiety, and generalized or substance-induced anxiety disorder.

The term "method of treating psychotic disorders" as used herein means relief from the symptoms or the prevention of psychotic disorders, which include, but are not limited to, schizophrenia, schizophreniform disorder, schizoaffective disorder, delusional disorder, brief psychotic disorder, shared psychotic disorder, psychotic disorder due to general medical condition, substance-induced psychotic disorder, or psychotic disorder not otherwise specified (*Diagnostic and Statistical Manual of Mental Disorders* (Ed. 4th) American Psychiatric Association, Washington, D.C. (1994)).

The term "method of treating convulsive disorders" means relief from the symptoms or the prevention of epilepsy, which include, but are not limited to, altered consciousness, altered motor activity, autonomic responses, inappropriate behavior patterns seizures including tonic or clonic jerking of extremities, emotional stress, sense of terror, uneasiness, nervousness, headache, fatigue, auditory hallucinations, aggressive outbursts, acute skeletal muscle spasm, and spasticity.

The term "method of treating depressive or bipolar disorders", as used herein, means relief from the symptoms or the prevention of depressive disorders, which include, but are not limited to, single-episode or recurrent major depressive disorder, seasonal affective disorder (SAD), dysthymic disorder, bipolar I and bipolar II manic disorders, and cyclothymic disorder.

The term "method of treating cognitive disorders" means relief from the symptoms or the prevention of cognitive disorders, which includes, but is not limited to delirium, dementia, amnesic disorders, and cognitive deficits, including age-related memory deficits, due to traumatic injury, stroke, Parkinson's disease, attention deficit disorder and Downs Syndrome. Any of these conditions may be attributable to substance abuse or withdrawal. Examples of dementia include dementia of the Alzheimer's type with early or late onset, and vascular dementia, any of which may be uncomplicated or accompanied by delirium, delusions or depressed mood; and dementia due to HIV virus, head trauma, Parkinson's disease or Creutzfeld-Jakob disease.

The term "method of treating sleeping disorders", as used herein, means relief from the symptoms or the prevention of sleep disorders or states that affect a subject's ability to sleep, which includes, but are not limited to, insomnia, sleep apnea, REM sleep interruptions, parasomnia, jet-lag syndrome, hypersomnia, shift workers' sleep disturbances, dysomnias, night terror, narcolepsy, disturbed sleep patterns, disturbed biological or circadian rhythms, sleep disturbances associated with such diseases as neurological disorders, neuropathic pain and restless leg syndrome, or providing sleep induction before surgical procedures or in disturbed or anxious states.

The term "method of treating neurodegenerative eye diseases", as used herein, means relief of symptoms or the prevention of neurodegenerative eye diseases, which includes, but is not limited to retinoschisis, vascular diseases of the retina, diseases caused by venous and/or arterial vascular occlusions, macular degenerations, traumatic retinal changes such as contusion of the eye, perforating eye injuries, siderosis/hemidosis, chalcosis, burns, retinopathia traumatica and/or injury to the retina from light, diseases of the choroid, diseases of the optic nerve, anterior ischemic optic neuropathy, optic atrophy, glaucoma, glaucoma simplex, secondary glaucoma and/or ocular hypertension.

The term "method of treating pain" means relief from the symptoms or the prevention of pain, which includes, but is not limited to, migraine, chronic back pain, phantom limb pain, neuropathic pain such as diabetic neuropathy, and post herpetic neuropathy.

The term "method of treating emesis" means relief from the symptoms or the prevention of emesis, which includes, but is not limited to, acute, delayed and anticipatory emesis, emesis induced by chemotherapy or radiation, as well as motion sickness, and post-operative nausea and vomiting.

The term "method of treating eating disorders" means relief from the symptoms or the prevention of eating disorders, which include, but are not limited to, anorexia nervosa, bulimia nervosa, obesity, weight-gain after smoking cessation, snacking and binge eating.

The term "benzodiazepine receptor" as used herein, includes the benzodiazepine receptor/GABA receptor/chloride channel complex (benzodiazepine receptor complex) and benzodiazepine receptor-agonist binding sites at or near the receptor complex. Both central nervous system ("central") and peripheral benzodiazepine receptors ("peripheral") are encompassed by the use of this term.

The term "$IC_{50}$" refers to the concentration causing a half-maximal inhibition of control specific binding.

In the compounds of the invention of formula I, $R^5$ is chosen from $C_1$ to $C_{20}$ hydrocarbon, substituted aryl, heterocyclyl and substituted heterocyclyl. Subgenera include compounds in which $R^5$ is $C_1$ to $C_{12}$ hydrocarbon or substituted aryl and those in which $R^5$ is a four, five, six or seven-membered heterocyclyl or substituted heterocyclyl. Preferred compounds include those in which $R^5$ is heteroaryl or substituted heteroaryl.

In compounds of formula II, A is chosen from a carbocycle, a heterocycle, a substituted carbocycle and a substituted heterocycle. Subgenera include compounds in which A is a carbocycle or substituted carbocycle and those in which A is a four, five, six, seven or eight-membered heterocyclyl or substituted heterocyclyl. Preferred compounds include those in which A is a four, five, six, seven or eight-membered lactam or substituted lactam, particularly an N-alkyl lactam. As is evident from inspection of the formula II, A is attached to the imidazopyridine through a carbon of A, not a heteroatom, if A is a heterocycle.

In compounds of formula I, m is one, two or three, preferably one. In compounds of formula II, n is zero, one or two, preferably zero.

Many of the compounds described herein contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, as well as their racemic and optically pure forms. Optically active (R)- and (S)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

The graphic representations of racemic, ambiscalemic and scalemic or enantiomerically pure compounds used herein are taken from Maehr, *J. Chem. Ed.* 62, 114-120 (1985): Solid and broken wedges are used to denote the absolute configuration of a chiral element; solid and broken bold lines are geometric descriptors indicating the relative configuration shown but denoting racemic character; and wedge outlines and dotted or broken lines denote enantiomerically pure compounds of indeterminate absolute configuration. Thus, the formula X is intended to encompass both of the pure enantiomers of that pair:

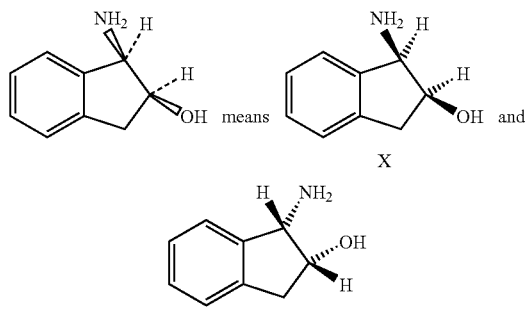

The following compounds are illustrative of the present invention, but the invention is in no way limited to the compounds listed herein: 2-(6-Methyl-2-p-tolyl-imidazo[1,2-a]pyridin-3-yl)-1-thiophen-2-yl-ethanone, 1-(6-Methyl-2-p-tolyl-imidazo[1,2-a]pyridin-3-yl)-3-thiophen-2-yl-propan-2-one, 1-(2,3-Dihydro-benzo[1,4]dioxin-2-yl)-2-(6-methyl-2-p-tolyl-imidazo[1,2-a]pyridin-3-yl)-ethanone, 1-(3-Methyl-3H-imidazol-4-yl)-2-(6-methyl-2-p-tolyl-imidazo[1,2-a]pyridin-3-yl)-ethanone, 1-(2,5-Dimethyl-2H-pyrazol-3-yl)-2-(6-methyl-2-p-tolyl-imidazo[1,2-a]pyridin-3-yl)-ethanone, 1-(1-Methyl-1H-pyrrol-2-yl)-2-(6-methyl-2-p-tolyl-imidazo[1,2-a]pyridin-3-yl)-ethanone, 1-(3-Methyl-thiophen-2-yl)-2-(6-methyl-2-p-tolyl-imidazo[1,2-a]pyridin-3-yl)-ethanone, 1-(2-Methyl-imidazo[1,2-a]pyridin-3-yl)-2-(6-methyl-2-p-tolyl-imidazo[1,2-a]pyridin-3-yl)-ethanone, 1-(3-Methoxy-thiophen-2-yl)-2-(6-methyl-2-p-tolyl-imidazo[1,2-a]pyridin-3-yl)-ethanone, 1-(1,5-Dimethyl-1H-[1,2,3]triazol-4-yl)-2-(6-methyl-2-p-tolyl-imidazo[1,2-a]pyridin-3-yl)-ethanone, 1-(5,7-Dimethyl-pyrazolo[1,5-a]pyrimidin-3-yl)-2-(6-methyl-2-p-tolyl-imidazo[1,2-a]pyridin-3-yl)-ethanone, 1-Cyclopentyl-2-(6-methyl-2-p-tolyl-imidazo[1,2-a]pyridin-3-yl)-ethanone, 1-(6-Methyl-2-p-tolyl-imidazo[1,2-a]pyridin-3-yl)-heptan-2-one, 1-(6-Methyl-2-p-tolyl-imidazo[1,2-a]pyridin-3-yl)-propan-2-one, 1-Methyl-3-(6-methyl-2-p-tolyl-imidazo[1,2-a]pyridin-3-yl)-piperidin-2-one, 1-Methyl-3-(6-methyl-2-p-tolyl-imidazo[1,2-a]pyridin-3-yl)-1,3,4,7-tetrahydro-azepin-2-one, 1-(6-Methyl-2-p-tolyl-imidazo[1,2-a]pyridin-3-yl)-4-phenyl-butan-2-one, 2-(6-Methyl-2-p-tolyl-imidazo[1,2-a]pyridin-3-yl)-1-thiophen-3-yl-ethanone, 2-[6-Chloro-2-(4-chloro-phenyl)-imidazo[1,2-a]pyridin-3-yl]-1-thiophen-2-yl-ethanone, 2-(6-Methyl-2-p-tolyl-imidazo[1,2-a]pyridin-3-yl)-1-(1,3,5-trimethyl-1H-pyrazol-4-yl)-ethanone, 1-Benzo[b]thiophen-2-yl-2-(6-methyl-2-p-tolyl-imidazo[1,2-a]pyridin-3-yl)-ethanone, 1-(4-Methyl-[1,2,3]thiadiazol-5-yl)-2-(6-methyl-2-p-tolyl-imidazo[1,2-a]pyridin-3-yl)-ethanone, 1-(3-Chloro-4-methanesulfonyl-thiophen-2-yl)-2-(6-methyl-2-p-tolyl-imidazo[1,2-a]pyridin-3-yl)-ethanone, 1-(1-Methyl-1H-imidazol-4-yl)-2-(6-methyl-2-p-tolyl-imidazo[1,2-a]pyridin-3-yl)-ethanone, 1-(5,7-Dimethyl-pyrazolo[1,5-a]pyrimidin-3-yl)-2-[2-(4-methoxy-phenyl)-6-methyl-imidazo[1,2-a]pyridin-3-yl]-ethanone, and 1-(2,7-Dimethyl-imidazo[1,2-a]pyridin-3-yl)-2-(6-methyl-2-p-tolyl-imidazo[1,2-a]pyridin-3-yl)-ethanone.

The corresponding chemical structures for the aforementioned compounds are as follows:

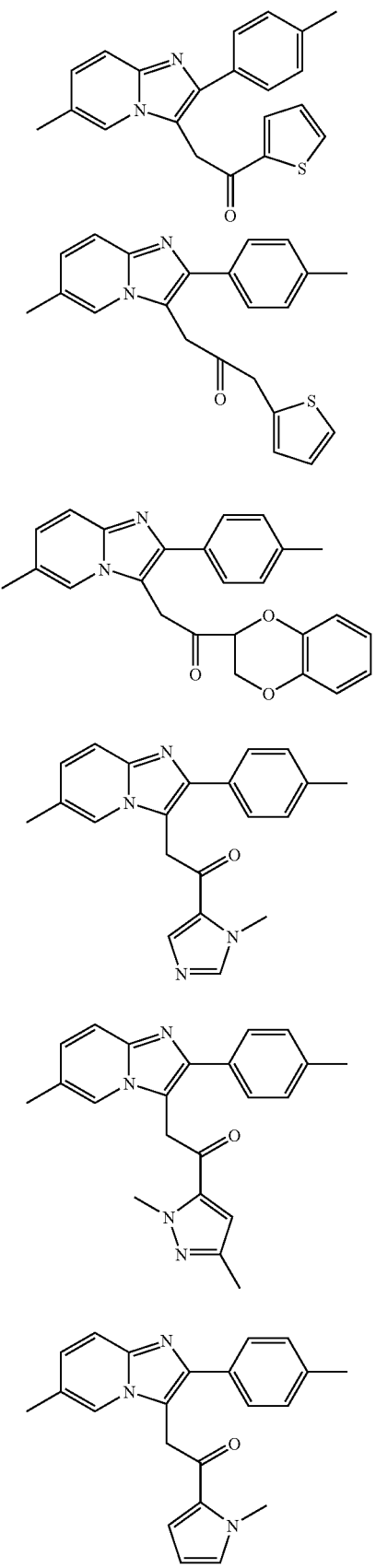

-continued
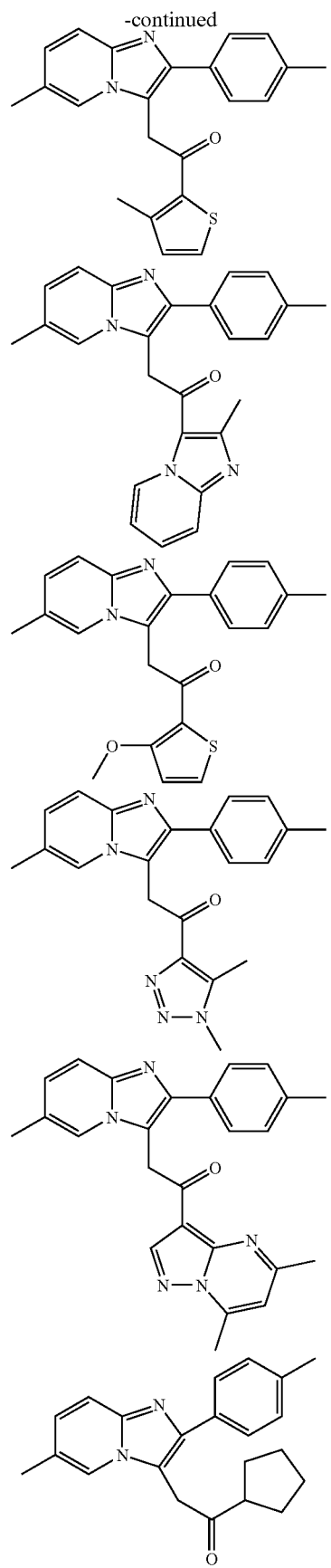
-continued
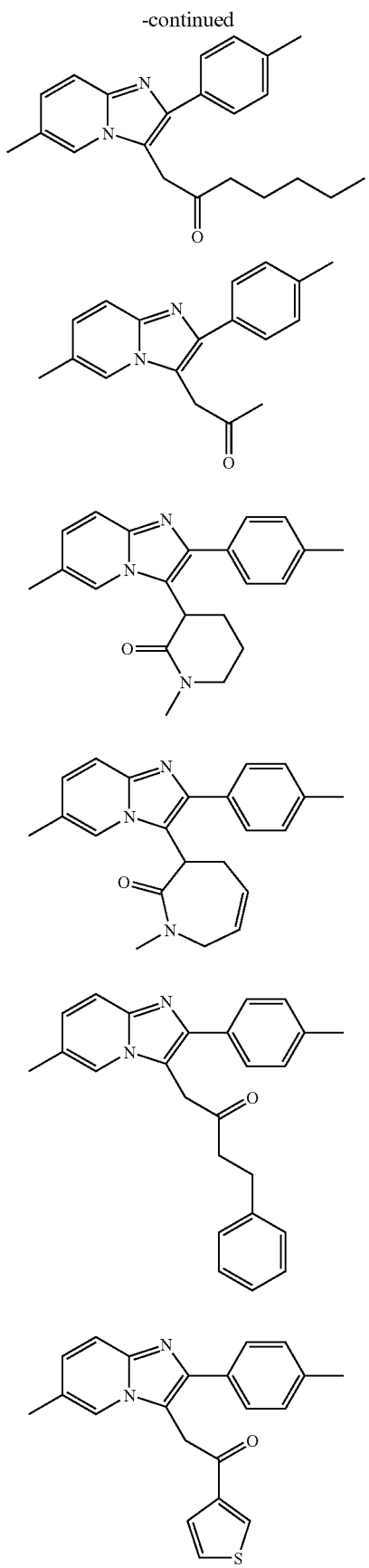

-continued

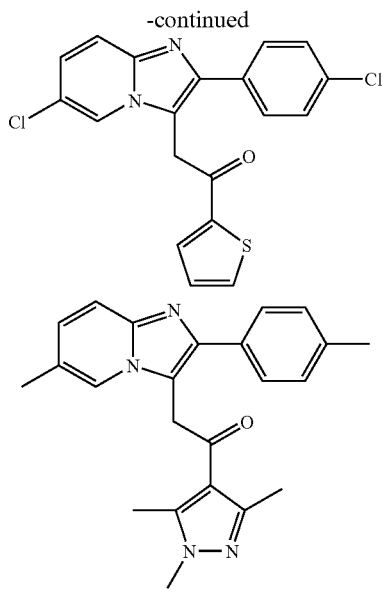

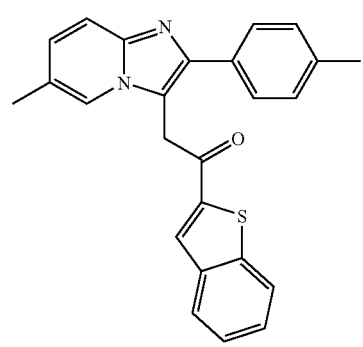

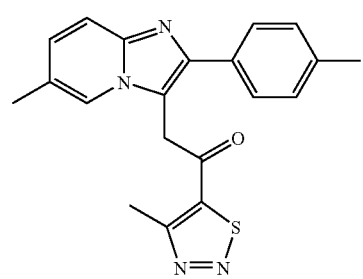

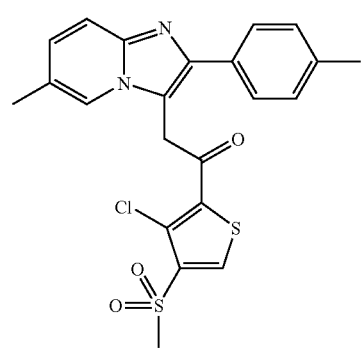

-continued

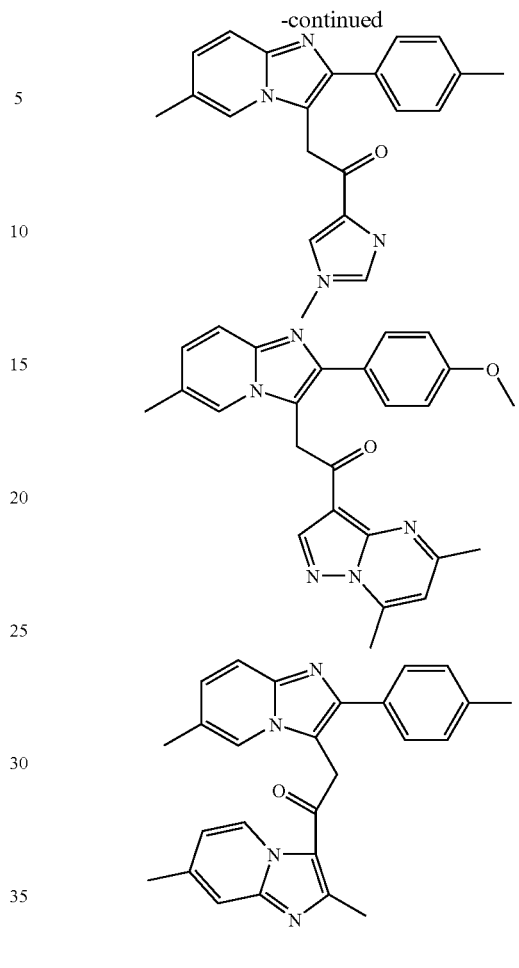

Of the compounds listed above, the following are preferred: 2-(6-Methyl-2-p-tolyl-imidazo[1,2-a]pyridin-3-yl)-1-thiophen-2-yl-ethanone, 1-(6-Methyl-2-p-tolyl-imidazo[1,2-a]pyridin-3-yl)-3-thiophen-2-yl-propan-2-one, 1-(2,3-Dihydro-benzo[1,4]dioxin-2-yl)-2-(6-methyl-2-p-tolyl-imidazo[1,2-a]pyridin-3-yl)-ethanone, 1-(3-Methyl-3H-imidazol-4-yl)-2-(6-methyl-2-p-tolyl-imidazo[1,2-a]pyridin-3-yl)-ethanone, 1-(2,5-Dimethyl-2H-pyrazol-3-yl)-2-(6-methyl-2-p-tolyl-imidazo[1,2-a]pyridin-3-yl)-ethanone, 1-(1-Methyl-1H-pyrrol-2-yl)-2-(6-methyl-2-p-tolyl-imidazo[1,2-a]pyridin-3-yl)-ethanone, 1-(3-Methyl-thiophen-2-yl)-2-(6-methyl-2-p-tolyl-imidazo[1,2-a]pyridin-3-yl)-ethanone, 1-(2-Methyl-imidazo[1,2-a]pyridin-3-yl)-2-(6-methyl-2-p-tolyl-imidazo[1,2-a]pyridin-3-yl)-ethanone, 1-(3-Methoxy-thiophen-2-yl)-2-(6-methyl-2-p-tolyl-imidazo[1,2-a]pyridin-3-yl)-ethanone, 1-(1,5-Dimethyl-1H-[1,2,3]triazol-4-yl)-2-(6-methyl-2-p-tolyl-imidazo[1,2-a]pyridin-3-yl)-ethanone, and 1-(5,7-Dimethyl-pyrazolo[1,5-a]pyrimidin-3-yl)-2-(6-methyl-2-p-tolyl-imidazo[1,2-a]pyridin-3-yl)-ethanone.

In general, the compounds of the present invention may be prepared by the methods illustrated in the reaction schemes as, for example, described below, or by modifications thereof, using readily available starting materials, reagents and conventional synthesis procedures. In these reactions, it is also possible to make use of variants that are in themselves known, but are not mentioned here. Compounds of the invention may be synthesized as follows.

General Procedure: Flash chromatography was performed on EM Science silica gel 60. Thin layer chromatography was performed using silica gel 60 $F_{254}$ plates, and compound visualization was effected using a UV light or with 10% $H_2SO_4$ containing 5% ammonium molybdate and 0.2% ceric sulfate. All reactions were carried out in oven-dried glassware under an argon atmosphere. $^1H$ NMR and $^{13}C$ NMR were performed on a 400 MHz Varian instrument. Tetramethylsilane (TMS), deuterated chloroform ($CDCl_3$) or deuterated dimethyl sulfoxide (DMSO-$d_6$) were used as internal standards for $^1H$ and $^{13}C$ spectra, respectively. J values are given in hertz.

Starting materials of structure type Y, for the following examples, are either commercially available from chemical suppliers, or may be synthesized following procedures known by those skilled in the art, such as those disclosed by Trapani et al. in *J. Med. Chem.* 40, 3109-18 (1997); by George et al. in U.S. Pat. No. 4,847,263, and by George and DePeretti in EP 0172097B1, which are hereby incorporated by reference. A representative example for which m=1 is shown below.

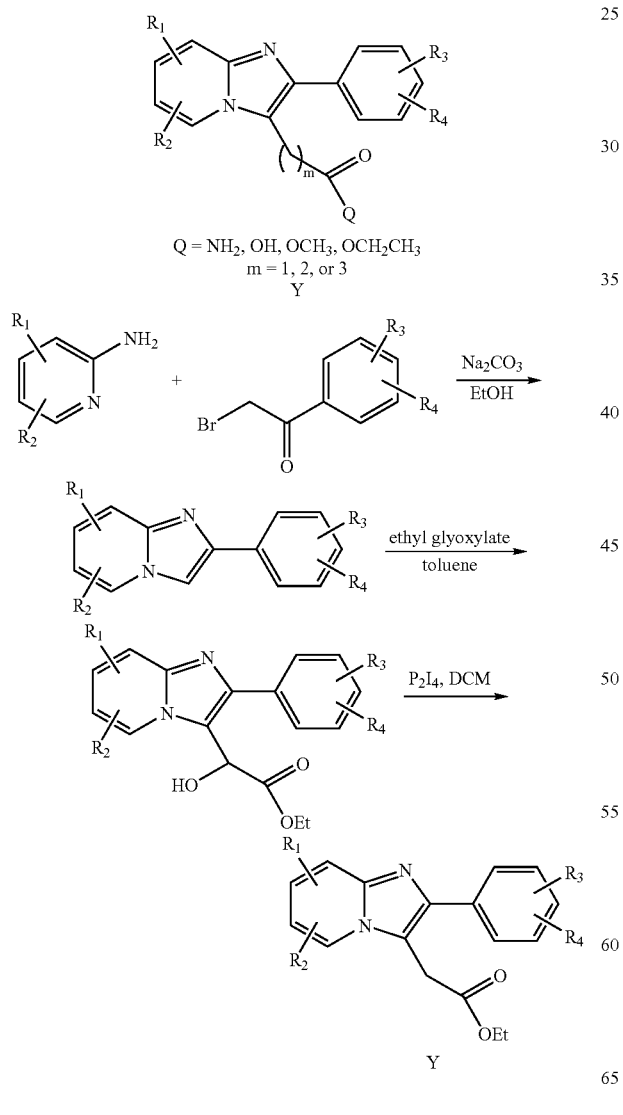

Method A (for the Synthesis of Ketones):

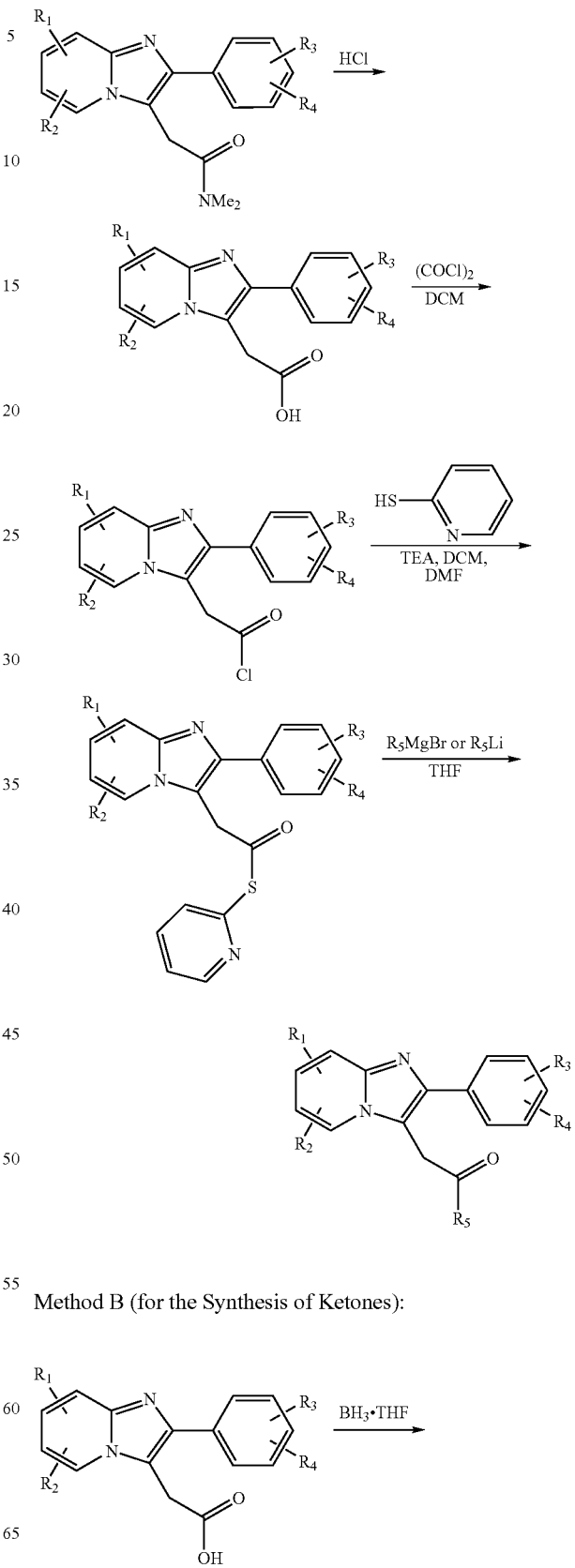

Method B (for the Synthesis of Ketones):

-continued

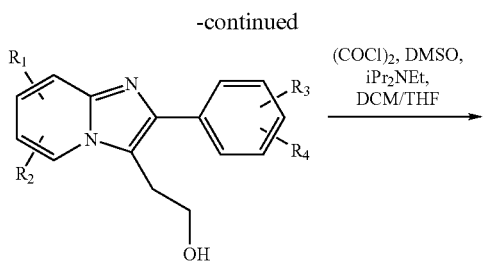

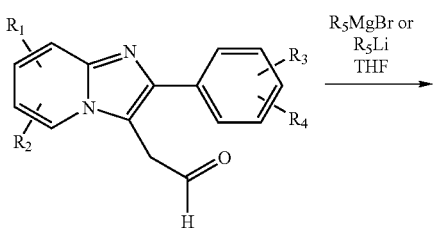

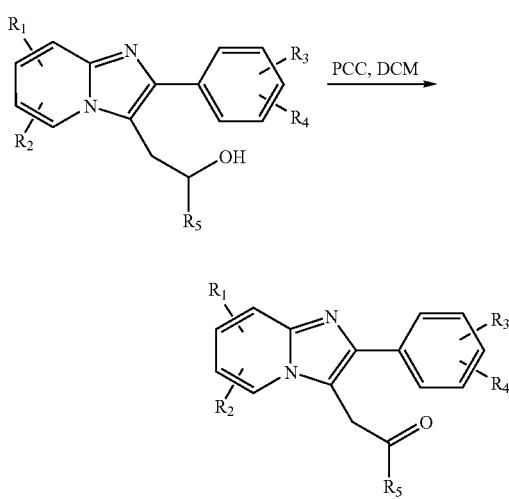

Method C (for the Synthesis of Ketones):

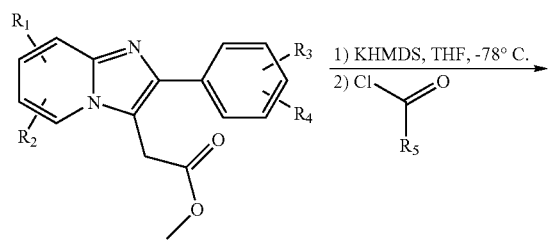

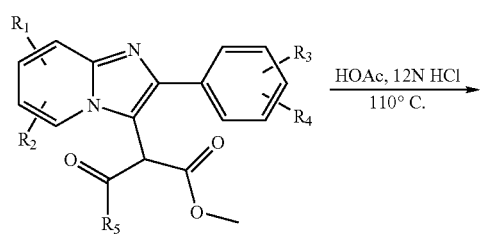

-continued

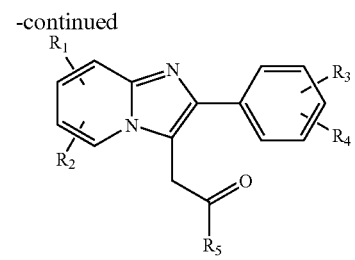

The invention is illustrated by the following Examples, but is not limited to the specific embodiments contained therein.

From Method A

Example 1a (6-Methyl-2-p-tolyl-imidazo[1,2-a]pyridin-3-yl)-acetic acid

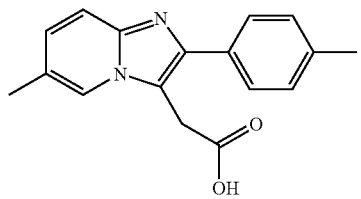

To a magnetically stirred solution of zolpidem (8.0 g, 26.0 mmol) at 0° C. under Ar atmosphere was added 6N HCl (80 mL). The reaction mixture was refluxed for 18 h. The mixture was cooled to 0° C., and 20% NaOH was added slowly to a pH of 6.5. The white solids were filtered in vacuo to provide the title compound (6.9 g, 94%) as a white solid. $^1$H NMR (DMSO-$d_6$) δ 2.30 (s, 3H), 2.35 (s, 3H), 3.94 (s, 2H), 7.10 (d, J=9.1 Hz, 1H), 7.25 (d, J=7.8 Hz, 2H), 7.48 (d, J=9.1 Hz, 1H), 7.72 (d, J=7.8 Hz, 2H), 8.18 (s, 1H). $^{13}$C-NMR (100 MHz, DMSO-$d_6$) δ 18.4, 21.4, 30.8, 114.8, 116.6, 121.6, 122.9, 127.9, 128.2, 129.8, 132.4, 137.3, 143.0, 143.5, 171.8.

Example 1b (6-Methyl-2-p-tolyl-imidazo[1,2-a]pyridin-3-yl)-acetyl chloride hydrochloride

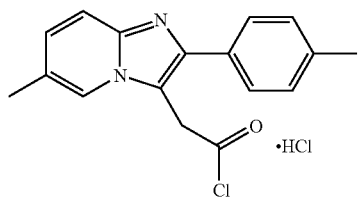

To a magnetically stirred solution of (6-methyl-2-p-tolyl-imidazo[1,2-a]pyridin-3-yl)-acetic acid 1a (1.0 g, 3.57 mmol) in dichloromethane (DCM) (10.0 mL) at 0° C. under Ar atmosphere were added dimethylformamide (DMF) (1 drop) and oxalyl chloride (0.467 mL, 5.35 mmol). The reaction mixture was stirred at 0° C. for 3 h, then concentrated in vacuo to provide the title compound (1.06 g, 100%) as a yellow solid. ¹H NMR (400 MHz, CDCl₃) δ 2.42 (s, 3H), 2.52 (s, 3H), 4.70 (s, 2H), 7.38 (d, J=7.3 Hz, 2H), 7.64 (m, 3H), 8.00 (s, 1H), 8.37 (d, J=8.0 Hz, 1H).

Example 1c (6-Methyl-2-p-tolyl-imidazo[1,2-a]pyridin-3-yl)-thioacetic acid S-pyridin-2-yl ester

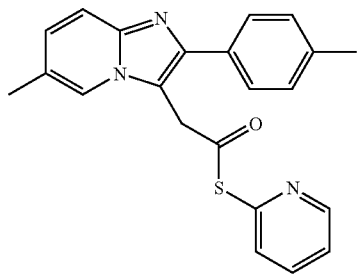

To a magnetically stirred solution of (6-methyl-2-p-tolyl-imidazo[1,2-a]pyridin-3-yl)-acetyl chloride 1b (6.22 g, 20.8 mmol) in dichloromethane (DCM) (62 mL) at 0° C. under Ar atmosphere were added 2-mercaptopyridine (2.54 g, 22.92 mmol) and triethylamine (TEA) (7.99 mL, 62.4 mmol). The reaction mixture was stirred for 2 h at 0° C. Water (50 mL) was added, and the aqueous phase was extracted with dichloromethane (2×300 mL). The combined organic layers were washed with water, dried (MgSO₄), and concentrated in vacuo to the crude product. The pure product was obtained by column chromatography over silica gel (20:80 EtOAc/hexanes, then 40:60 EtOAc/hexanes as eluent) which gave the title compound (4.71 g, 60%) as a yellow solid. ¹H NMR (400 MHz, CDCl₃) δ 2.36 (s, 3H), 2.41 (s, 3H), 4.34 (s, 2H), 7.09 (d, J=1.4 Hz, 1H), 7.29 (m, 3H), 7.59 (t, J=1.1 Hz, 2H), 7.70 (m, 3H), 7.80 (s, 1H), 8.63 (m, 1H).

Example 1d 2-(6-Methyl-2-p-tolyl-imidazo[1,2-a]pyridin-3-yl)-1-thiophen-2-yl-ethanone

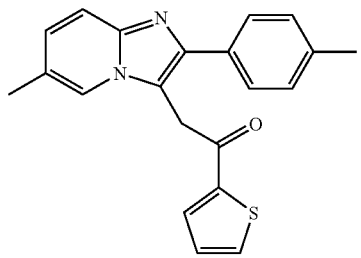

To a magnetically stirred solution of (6-methyl-2-p-tolyl-imidazo[1,2-a]pyridin-3-yl)-thioacetic acid S-pyridin-2-yl ester 1c (2.0 g, 5.36 mmol) in tetrahydrofuran (THF) (10 mL) at 0° C. under Ar atmosphere was added thiophen-2-yl-magnesium bromide (5.89 mL, 1.0 M in THF). The reaction mixture was stirred for 18 h at 0° C. Aqueous 10% NaOH solution (50 mL) was added, and the aqueous phase was extracted with ethylacetate (EtOAc) (2×100 mL). The combined organic layers were washed with water, dried (MgSO₄), and concentrated in vacuo to the crude product. The pure product was obtained by column chromatography over silica gel (20:80 EtOAc/hexanes, then 50:50 EtOAc/hexanes as eluent) which gave the title compound (0.26 g, 14%) as a yellow solid. ¹H NMR (400 MHz, CDCl₃) δ 2.31 (s, 3H), 2.39 (s, 3H), 4.61 (s, 2H), 7.07 (m, 2H), 7.25 (d, J=7.7 Hz, 2H), 7.55 (m, 3H), 7.63 (d, J=3.7 Hz, 1H), 7.65 (d, J=5.1 Hz, 1H), 7.77 (s, 1H). ¹³C NMR (100 MHz, CDCl₃) δ 18.6, 21.5, 35.8, 112.9, 117.0, 121.7, 122.2, 127.8, 128.6, 128.6, 129.6, 131.8, 133.2, 134.9, 137.8, 142.8, 144.5, 144.9, 188.2. Mass spectrum m/e 347 (M⁺.

Example 2d 1-(6-Methyl-2-p-tolyl-imidazo[1,2-a]pyridin-3-yl)-propan-2-one

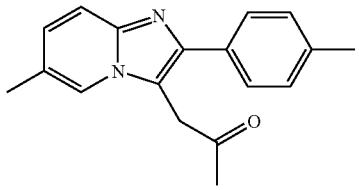

Prepared from (6-methyl-2-p-tolyl-imidazo[1,2-a]pyridin-3-yl)-thioacetic acid S-pyridin-2-yl ester 1c and methyl magnesium bromide (MeMgBr) using a similar procedure described above. ¹H NMR (400 MHz, CDCl₃) δ 2.14 (s, 3H), 2.31 (s, 3H), 2.38 (s, 3H), 4.08 (s, 2H), 7.03 (d, J=9.1 Hz, 1H), 7.25 (d, J=7.7 Hz, 2H), 7.54 (m, 4H). Mass spectrum m/e 279 (M⁺).

Example 3d 1-(4-Chloro-phenyl)-2-(6-methyl-2-p-tolyl-imidazo[1,2-a]pyridin-3-yl)-ethanone

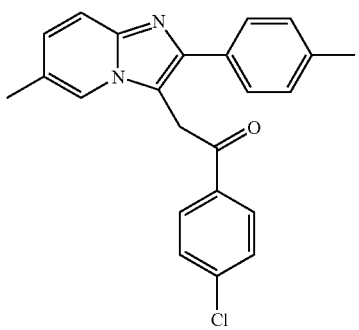

Prepared from (6-methyl-2-p-tolyl-imidazo[1,2-a]pyridin-3-yl)-thioacetic acid S-pyridin-2-yl ester 1c and 4-chlorophenylmagnesium bromide using a similar procedure described above. ¹H NMR (400 MHz, CDCl₃) δ 2.29 (s, 3H), 2.38 (s, 3H), 4.61 (s, 2H), 7.02 (d, J=9.8 Hz, 1H), 7.23 (d, J=8.0 Hz, 2H), 7.36 (d, J=8.8 Hz, 2H), 7.51 (t, J=9.1 Hz, 3H), 7.65 (s, 1H), 7.84 (d, J=8.4 Hz, 2H). Mass spectrum m/e 375 (M+).

Example 4d 2-(6-Methyl-2-p-tolyl-imidazo[1,2-a]pyridin-3-yl)-1-phenyl-ethanone

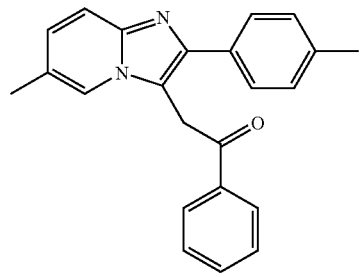

Prepared from (6-methyl-2-p-tolyl-imidazo[1,2-a]pyridin-3-yl)thioacetic acid S-pyridin-2-yl ester 1c and phenylmagnesium bromide using a similar procedure described above. $^1$H NMR (400 MHz, CDCl$_3$) δ 2.26 (s, 3H), 2.37 (s, 3H), 4.64 (s, 2H), 7.00 (d, J=8.8 Hz, 1H), 7.21 (d, J=8.0 Hz, 2H), 7.41 (t, J=7.7 Hz, 2H), 7.52 (d, J=8.4 Hz, 2H), 7.58 (m, 3H), 7.96 (d, J=7.3 Hz, 2H). Mass spectrum m/e 341 (M+).

Example 5d 1-(6-Methyl-2-p-tolyl-imidazo[1,2-a]pyridin-3-yl)-heptan-2-one

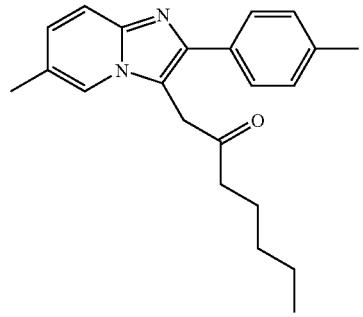

Prepared from (6-methyl-2-p-tolyl-imidazo[1,2-a]pyridin-3-yl)-thioacetic acid S-pyridin-2-yl ester 1c and pentylmagnesium bromide using a similar procedure described above. $^1$H NMR (400 MHz, CDCl$_3$) δ 0.81 (t, 3H), 1.17 (m, 6H), 1.51 (m, 2H), 2.28 (s, 3H), 2.37 (s, 3), 4.04 (s, 2H), 7.00 (d, J=8.4 Hz, 1H), 7.23 (d, J=7.3 Hz, 2H), 7.55 (m, 4H). Mass spectrum m/e 335 (M+).

The following compound was also synthesized according to Method A, and in vitro data for this compound is shown in Table 1b.

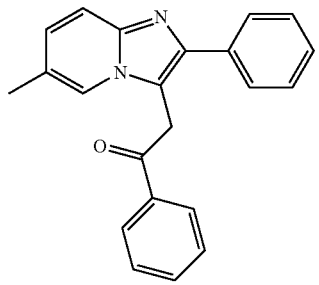

From Method B

Example 6a 2-(6-Methyl-2-p-tolyl-imidazo[1,2-a]pyridin-3-yl)-ethanol

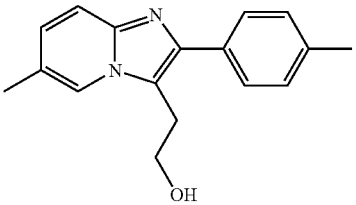

To a mechanically stirred suspension of (6-methyl-2-p-tolyl-imidazo[1,2-a]pyridin-3-yl)-acetic acid 1a (5.0 g, 17.9 mmol) in THF (50 ml) at 0° C. under nitrogen atmosphere was added dropwise a 1.0 M solution of borane-tetrahydrofuran complex (56 ml, 56 mmol). The mixture was slowly warmed to ambient temperature and stirred for 2 h (nearly homogeneous at this point, slightly hazy). The reaction was quenched with 1.0 N HCl at 0° C., and stirred at ambient temperature for 0.5 h. The solution was concentrated in vacuo in order to remove the volatiles. The resulting solution was basified at 0° C. with 10% NaOH and extracted with dichloromethane (2×250 ml). The organic layers were combined, dried (Na$_2$SO$_4$), and concentrated to afford 4.4 g (93%) of product as a white solid. $^1$H NMR (400 MHz, CDCl$_3$) δ 1.80 (broad s, 1H), 2.29 (s, 3H), 2.37 (s, 3H), 3.21 (t, J=6.2 Hz, 2H), 4.00 (t, J=6.2 Hz, 2H), 6.82 (dd, J=1.5, 8.8 Hz, 1H), 7.14 (d, J=8.0 Hz, 2H), 7.29 (d, J=9.1 Hz, 1H), 7.58 (d, J=8.0 Hz, 2H), 7.84 (s, 1H).

Example 6b (6-Methyl-2-p-tolyl-imidazo[1,2-a]pyridin-3-yl)-acetaldehyde

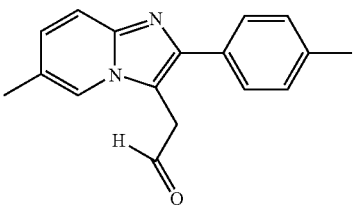

To a magnetically stirred solution of oxalyl chloride (COCl)$_2$ (0.8 ml, 9.2 mmol) in dichloromethane (20 ml) at −78° C. under nitrogen atmosphere was added dimethyl sulfoxide (DMSO) (1.1 ml, 15.5 mmol). The reaction mixture was stirred for 30 minutes at −78° C. To this mixture was added 2-(6-methyl-2-p-tolyl-imidazo[1,2-a]pyridin-3-yl)-ethanol 6a (2.0 g, 7.5 mmol) as a slurry in three portions using 60 ml (2×20 ml) of anhydrous THF. The mixture was stirred at −78° C. for 0.5 h, then N,N-diisopropylethylamine (iPr₂NEt) (6.7 ml, 38.5 mmol) was added at −78° C. The suspension was warmed to 0° C. and stirred at this temperature for 1 h. (A homogeneous tan solution was obtained within 10-15 minutes). The reaction was quenched at 0° C. with deionized water (DI) (50 ml). The aqueous phase was extracted with 400 ml of EtOAc (2×200 ml). The organic streams were combined, dried (MgSO$_4$) and concentrated in vacuo to afford the crude product as a brown foam. The pure product was obtained by column chromatography over silica gel (20:80 EtOAc/hexanes, then 80:20 EtOAc/hexanes as eluent), which gave the title compound (0.84 g, 42%) as a yellow solid. $^1$H NMR (400 MHz, CDCl$_3$) δ 2.33 (s, 3H), 2.39 (s, 3H), 4.11 (s, 2H), 7.07 (dd, J=1.5, 9.1 Hz, 1H), 7.26 (d, J=7.3 Hz, 2H), 7.58 (m, 4H), 9.74 (s, 1H).

Example 6c 2-(6-Methyl-2-p-tolyl-imidazo[1,2-a]pyridin-3-yl)-1-thiophen-2-yl-ethanol

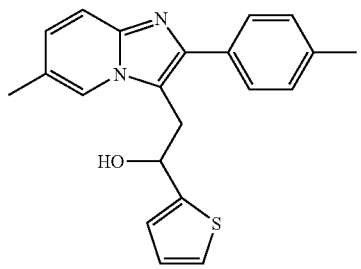

To a magnetically stirred −78° C. solution of thiophene magnesium bromide (7.9 mL, 7.95 mmol, 1M solution in THF) was added a solution of aldehyde 6b (2.65 mmol) in THF (15 mL). The reaction mixture was slowly (over 1 h) warmed to 0° C. and stirred for 2 h. It was then quenched with water. The volatiles were removed in vacuo and the aqueous phase was extracted with methylene chloride (2×100 mL). The combined organic phases were dried over sodium sulfate and concentrated to afford crude product as an oil. The pure product was obtained by column chromatography over silica gel (20:80 EtOAc/hexanes, then 60:40 EtOAc/hexanes as eluent), which gave the title compound (0.55 g, 62%) as a white solid. $^1$H NMR (400 MHz, CDCl$_3$) δ 2.28 (s, 3H), 2.37 (s, 3H), 3.35 (m, 2H), 5.25 (m, 1H), 6.75 (d, J=9.1 Hz, 1H), 6.98 (dd, J=3.6, 9.1 Hz, 2H), 7.05 (m, 3H), 7.29 (dd, J=1.0, 4.7 Hz, 1H), 7.48 (d, J=8.0 Hz, 2H), 7.48 (d, J=8.0 Hz, 1H).

Example 6d 2-(6-Methyl-2-p-tolyl-imidazo[1,2-a]pyridin-3-yl)-1-thiophen-2-yl-ethanone

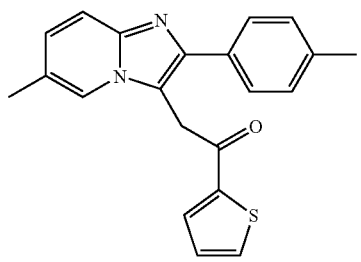

To a magnetically stirred solution of pyridinium chlorochromate (PCC) (0.90 g, 4.18 mmol), sodium acetate (0.38 g, 4.63 mmol), and 4 Å molecular sieves (0.38 g) in dichloromethane (DCM) (100 mL) at 0° C. under Ar atmosphere was added 2-(6-methyl-2-p-tolyl-imidazo[1,2-a]pyridin-3-yl)-1-thiophen-2-yl-ethanol 6c (0.70 g mL, 2.01 mmol). The reaction mixture was stirred for 0.5 h at 0° C., then warmed to room temperature and stirred for 3 h. Water (100 mL) was added, and the aqueous phase was extracted with dichloromethane (100 mL). The combined organic layers were washed with water (2×100 mL), dried (MgSO$_4$), and concentrated in vacuo to the crude product. The pure product was obtained by column chromatography over silica gel (80:20 dichloromethane/EtOAc, as eluent), which gave the title compound (0.26 g, 36%) as an off white solid. $^1$H NMR (400 MHz, CDCl$_3$) δ 2.31 (s, 3H), 2.39 (s, 3H), 4.61 (s, 2H), 7.07 (m, 2H), 7.25 (d, J=7.7 Hz, 2H), 7.55 (m, 3H), 7.63 (d, J=3.7 Hz, 1H), 7.65 (d, J=5.1 Hz, 1H), 7.77 (s, 1H). $^{13}$C NMR (100 MHz, CDCl$_3$) δ 18.6, 21.5, 35.8, 112.9, 117.0, 121.7, 122.2, 127.8, 128.6, 128.6, 129.6, 131.8, 133.2, 134.9, 137.8, 142.8, 144.5, 144.9, 188.2. Mass spectrum m/e 347 (M$^+$).

Example 7d

1-Cyclopentyl-2-(6-methyl-2-p-tolyl-imidazo[1,2-a]pyridin-3-yl)-ethanone

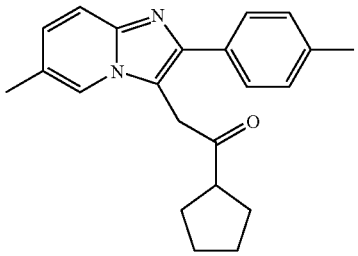

Prepared from PCC oxidation of the alcohol obtained from the reaction of (6-methyl-2-p-tolyl-imidazo[1,2-a]pyridin-3-yl)-acetaldehyde 6b and cyclopentylmagnesium bromide using a similar procedure described above. $^1$H NMR (400 MHz, CDCl$_3$) δ 1.53 (m, 8H), 2.33 (s, 3H), 2.39 (s, 3H), 2.93 (m, 1H), 4.15 (s, 2H), 7.04 (d, J=9.1 Hz, 1H), 7.25 (d, J=7.7 Hz, 2H), 7.55 (m, 4H).

Example 8D

3-Methyl-1-(6-methyl-2-p-tolyl-imidazo[1,2-a]pyridin-3-yl)-butan-2-one

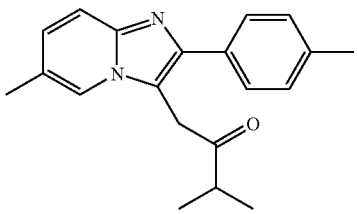

Prepared from PCC oxidation of the alcohol obtained from the reaction of (6-methyl-2-p-tolyl-imidazo[1,2-a]pyridin-3-yl)-acetaldehyde 6b and isopropylmagnesium bromide using a similar procedure described above. $^1$H NMR (400 MHz, CDCl₃) δ 1.10 (d, J=7.0 Hz, 6H), 2.32 (s, 3H), 2.39 (s, 3H), 2.72 (m, 1H), 4.15 (s, 2H), 7.04 (d, J=9.2 Hz, 1H), 7.25 (d, J=8.0 Hz, 2H), 7.54 (m, 4H).

Example 9d

1-Cyclopropyl-2-(6-methyl-2-p-tolyl-imidazo[1,2-a]pyridine-3-yl)-ethanone

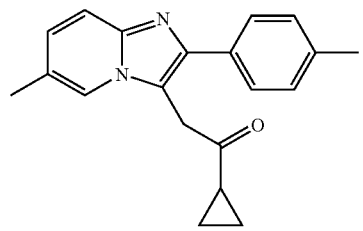

Prepared from PCC oxidation of the alcohol obtained from the reaction of (6-methyl-2-p-tolyl-imidazo[1,2-a]pyridin-3-yl)-acetaldehyde 6b and cyclopropylmagnesium bromide using a similar procedure described above. ¹H NMR (400 MHz, CDCl₃) δ 0.85 (m, 2H), 1.07 (m, 2H), 1.93 (m, 1H), 2.33 (s, 3H), 2.40 (s, 3H), 4.22 (s, 2H), 7.05 (d, J=9.1 Hz, 1H), 7.27 (d, J=8.1 Hz, 2H), 7.54 (d, J=9.1 Hz, 1H), 7.60 (d, J=8.0 Hz, 3H).

Example 10d 2-(6-Methyl-2-p-tolyl-imidazo[1,2-a]pyridin-3-yl)-1-(1,3,5-trimethyl-1H-pyrazol-4-yl)-ethanone

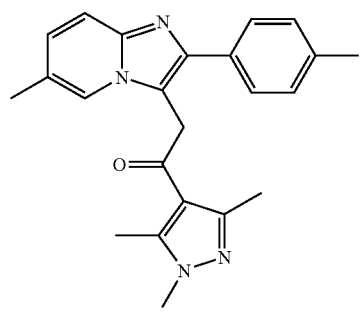

Prepared from PCC oxidation of the alcohol obtained from the reaction of (6-methyl-2-p-tolyl-imidazo[1,2-a]pyridin-3-yl)-acetaldehyde 6b and 1,3,5-trimethyl-1H-pyrazolyl magnesium bromide using a similar procedure described above. ¹H NMR (400 MHz, CDCl₃) δ2.33 (s, 3H), 2.38 (s, 3H), 2.52 (s, 3H), 2.53 (s, 3H), 3.78 (s, 3H), 4.43 (s, 2H), 7.04 (d, J=8.8 Hz, 1H), 7.22 (m, 3H), 7.57 (m, 3H). Mass spectrum m/e 373 (M⁺.

Example 11d

1-Furan-3-yl-2-(6-methyl-2-p-tolyl-imidazo[1,2-a]pyridin-3-yl)-ethanone

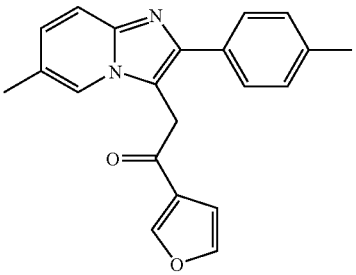

Prepared from PCC oxidation of the alcohol obtained from the reaction of (6-methyl-2-p-tolyl-imidazo[1,2-a]pyridin-3-yl)-acetaldehyde 6b and furanyl magnesium bromide using a similar procedure described above. ¹H NMR (400 MHz, CDCl₃) δ2.33 (s, 3H), 2.41 (s, 3H), 4.46 (s, 2H), 6.72 (dd, J=1.8, 0.7 Hz, 1H), 7.06 (dd, J=9.1 Hz, 1H), 7.28 (d, J=7.7 Hz, 2H), 7.40 (t, J=1.4 Hz, 1H), 7.57 (m, 3H), 7.78 (s, 2H). Mass spectrum m/e 331 (M⁺).

Example 12d 1-(6-Methyl-2-p-tolyl-imidazo[1,2-a]pyridin-3-yl)-4-phenyl-butan-2-one

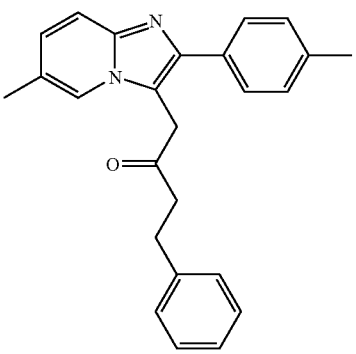

Prepared from PCC oxidation of the alcohol obtained from the reaction of (6-methyl-2-p-tolyl-imidazo[1,2-a]pyridin-3-yl)-acetaldehyde 6b and ethylphenyl magnesium bromide using a similar procedure described above. ¹H NMR (400 MHz, CDCl₃) δ2.29 (s, 3H), 2.40 (s, 3H), 2.76 (t, J=7.3 Hz, 2H), 2.87 (t, J=7.3 Hz, 2H), 4.05 (s, 2H), 7.04 (m, 3H), 7.22 (m, 5H), 7.44 (s, 1H), 7.52 (m, 3H). Mass spectrum m/e 369 (M⁺).

The following compounds were also synthesized according to Method B, and in vitro data for these compounds are shown in Tables 1a or Table 1b.

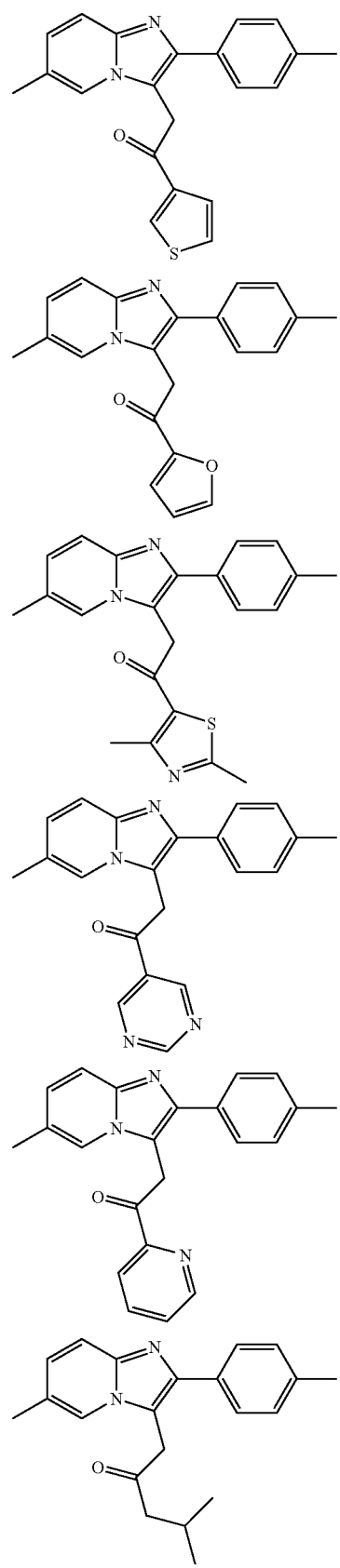
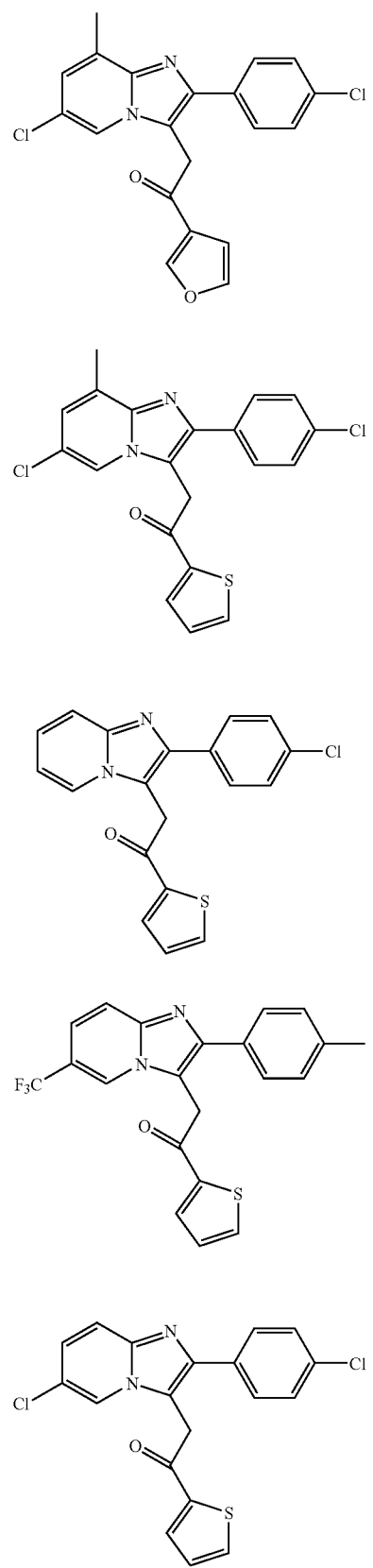

From Method C

Example 13a 2-(4-Methoxy-phenyl)-6-methyl-imidazo[1,2-a]pyridine

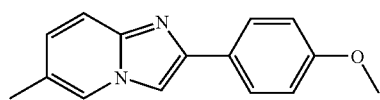

To a magnetically stirred solution of 2-bromo-1-(4-methoxy-phenyl)-ethanone (3.0 g, 13.09 mmol) and 5-methylpyridin-2-ylamine (1.42 g, 13.09 mmol) in EtOH (30 mL) under Ar atmosphere was added sodium carbonate (2.77 g, 26.18 mmol). The reaction mixture was refluxed for 4 h. The mixture was cooled to room temperature and concentrated in vacuo. Water (60 mL) was added, and the aqueous phase was extracted with dichloromethane (100 mL). The combined organic layers were washed with water (100 mL), dried (MgSO$_4$), and concentrated in vacuo to provide the title compound (2.8 g, 90%) as a white solid. $^1$H NMR (400 MHz, CDCl$_3$) δ 2.27 (s, 3H), 3.82 (s, 3H), 6.95 (m, 3H), 7.48 (d, J=8.8 Hz, 1H), 7.65 (s, 1H), 7.85 (m, 3H).

Example 13b

Hydroxy-[2-(4-methoxy-phenyl)-6-methyl-imidazo[1,2-a]pyridin-3-yl]-acetic acid ethyl ester

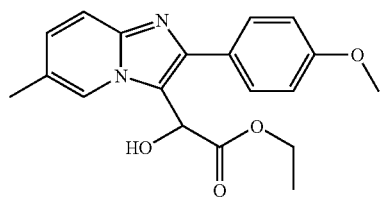

To a magnetically stirred solution of 2-(4-methoxy-phenyl)-6-methyl-imidazo[1,2-a]pyridine 13a (2.55 g, 10.71 mmol) and ethyl glyoxylate toluene solution (11.79 mL, 54.62 mmol) in toluene (130 mL) under Ar atmosphere was added p-toluenesulfonic acid monohydrate (60.9 mg, 0.32 mmol). The reaction mixture was equipped with a dean-stark trap and refluxed for 4 h. The mixture was cooled to room temperature and concentrated in vacuo. The crude product was purified by column chromatography over silica gel (40:60 EtOAc/hexane, then 100% EtOAc as eluent), which gave the title compound (0.72 g, 20%) as an off white solid. $^1$H NMR (400 MHz, CDCl$_3$) δ1.15 (t, J=7.0 Hz, 3H), 2.31 (s, 3H), 3.83 (s, 3H), 4.13 (m, 1H), 4.24 (m, 1H), 5.75 (s, 1H), 6.91 (d, J=8.8 Hz, 2H), 7.04 (dd, J=1.4, 9.1 Hz, 1H), 7.47 (d, J=9.1 Hz, 1H), 7.60 (d, J=8.8 Hz, 2H), 7.99 (s, 1H).

Example 13c

[2-(4-Methoxy-phenyl)-6-methyl-imidazo[1,2-a]pyridin-3-yl]-acetic acid ethyl ester

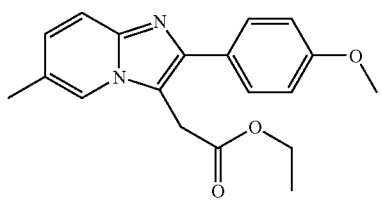

To a magnetically stirred solution of hydroxy-[2-(4-methoxy-phenyl)-6-methyl-imidazo[1,2-a]pyridin-3-yl]-acetic acid ethyl ester 13b (0.72 g, 2.11 mmol) in DCM (21 mL) under Ar atmosphere was added P$_2$I$_4$ (0.84 g mg, 1.48 mmol). The reaction mixture was stirred at room temperature for 4 h. Aqueous NaH$_2$CO$_3$ (100 mL) was added, and the aqueous phase was extracted with dichloromethane (20 mL). The combined organic layers were washed with water (100 mL), dried (MgSO$_4$), and concentrated in vacuo to the crude product. The pure product was obtained by column chromatography over silica gel (40:60 EtOAc/hexane, then 100% EtOAc as eluent), which gave the title compound (0.29 g, 42%) as an off white solid. $^1$H NMR (400 MHz, CDCl$_3$) δ 1.25 (t, J=7.3 Hz, 3H), 2.33 (s, 3H), 3.82 (s, 3H), 3.96 (s, 2H), 4.19 (q, J=7.3 Hz, 2H), 6.97 (d, J=8.8 Hz, 2H), 7.04 (dd, J=1.4, 9.1 Hz, 1H), 7.53 (d, J=9.1 Hz, 1H), 7.73 (d, J=8.8 Hz, 2H), 7.85 (s, 1H).

Example 13d 1-(5,7-Dimethyl-pyrazolo[1,5-a]pyrimidin-3-yl)-2-[2-(4-methoxy-phenyl)-6-methyl-imidazo[1,2-a]pyridin-3-yl]-ethanone

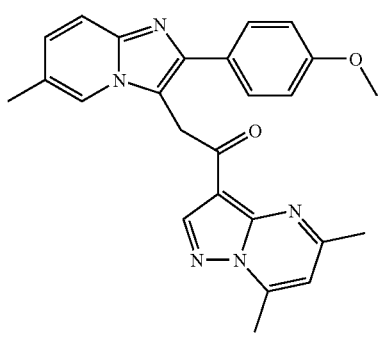

To a magnetically stirred solution of [2-(4-methoxy-phenyl)-6-methyl-imidazo[1,2-a]pyridin-3-yl]-acetic acid ethyl ester 13c (0.075 g, 0.231 mmol) in THF (3.0 mL) at −78° C. under Ar atmosphere was added potassium bis(trimethylsilyl) amide (KHMDS) (0.508 mL, 0.5M, 0.254 mmol). The reaction mixture was stirred for 15 min at −78° C., then a THF solution of 5,7-dimethyl-pyrazolo[1,5-a]pyrimidine-3-carbonyl chloride (0.053 g, 0.254 mmol) was added. After an additional 60 min at −78° C., water (20 mL) was added, and the reaction mixture was warmed to room temperature. Water was added, and the aqueous phase was extracted with ethyl acetate (2×100 mL). The combined organic layers were washed with water, dried (MgSO$_4$), and concentrated in vacuo to the crude alkylated product. The crude adduct was dissolved in acetic acid (HOAc) (1 mL) and 12 N HCl (1 mL). The reaction mixture refluxed for 2 h. The mixture was cooled to room temperature and treated with aq $Na_2CO_3$ solution until basic. The aqueous solution was extracted with dichloromethane (2×50 mL). The combined organic layers were washed with water (20 mL), dried ($MgSO_4$), and concentrated in vacuo to the crude product. The pure product was obtained by column chromatography over silica gel, (40:60 EtOAc/hexane, then 100% EtOAc as eluent), which gave the title compound (0.02 g, 20%) as an off white solid. $^1$H NMR (400 MHz, $CDCl_3$) δ2.28 (s, 3H), 2.62 (s, 3H), 2.82 (s, 3H), 3.81 (s, 3H), 4.98 (s, 2H), 6.80 (s, 1H), 6.91 (d, J=8.4 Hz, 2H), 7.02 (d, J=9.1 Hz, 1H), 7.54 (d, J=9.1 Hz, 1H), 7.68 (d, J=9.0 Hz, 2H), 7.76 (s, 1H), 8.62 (s, 1H). Mass spectrum m/e 426 ($M^+$).

Example 14d 2-(6-chloro-2-phenyl-imidazo[1,2-a]pyridin-3-yl)-1-thiophen-2-yl-ethanone

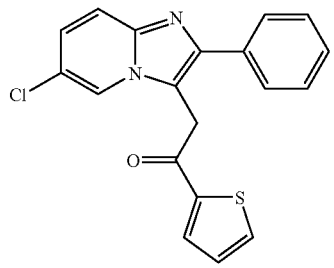

Prepared from the decarboxylation of the ethyl ester obtained by the reaction of (6-chloro-2-phenyl-imidazo[1,2-a]pyridin-3-yl)-acetic acid ethyl ester and 1-thiophene-2-carbonyl chloride using a procedure similar to that described in Example 13. $^1$H NMR (400 MHz, $CDCl_3$) δ4.64 (s, 2H), 7.12 (dd, J=3.7, 4.8 Hz, 1H), 7.20 (dd, J=1.8, 9.5 Hz, 1H), 7.45 (m, 3H), 7.67 (m, 5H), 8.09 (d, J=1.5 Hz, 1H). Mass spectrum m/e 353 ($M^+$).

Example 15d 1-(3-Methyl-3H-imidazol-4-yl)-2-(6-methyl-2-p-tolyl-imidazo[1,2-a]pyridin-3-yl)-ethanone

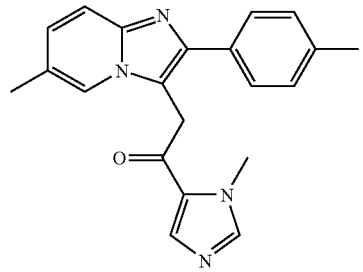

Prepared from the decarboxylation of the methyl ester obtained by the reaction of (6-methyl-2-p-tolyl imidazo[1,2-a]pyridin-3-yl)acetic acid methyl ester (from Example 35a) and 3-methyl-3H-imidazol-4-carbonyl chloride using a procedure similar to that described in Example 13. $^1$H NMR (400 MHz, $CDCl_3$) δ2.34 (s, 3H), 2.39 (s, 3H), 3.91 (s, 3H), 4.52 (s, 2H), 7.05 (dd, J=1.1, 9.1 Hz, 1H), 7.26 (m, 2H), 7.57 (m, 4H), 7.74 (s, 1H), 7.80 (s, 1H). Mass spectrum m/e 345 ($M^+$).

Example 16d 1-(3-Chloro-thiophen-2-yl)-2-(6-methyl-2-p-tolyl-imidazo[1,2-a]pyridin-3-yl)-ethanone

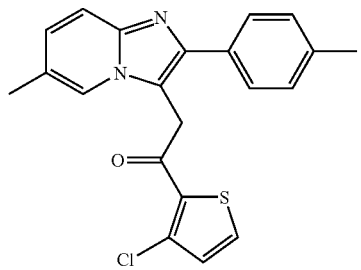

Prepared from the decarboxylation of the methyl ester obtained by the reaction of (6-methyl-2-p-tolyl imidazo[1,2-a]pyridin-3-yl)acetic acid methyl ester 35a and 3-chloro-thiophen-2-carbonyl chloride using a procedure similar to that described in Example 13. $^1$H NMR (400 MHz, $CDCl_3$) δ 2.32 (s, 3H), 2.38 (s, 3H), 4.75 (s, 2H), 7.05 (dd, J=1.4, 9.1 Hz, 1H), 7.10 (d, J=5.5 Hz, 1H), 7.24 (m, 2H), 7.55 (m, 4H), 7.63 (d, J=5.5 Hz, 1H). Mass spectrum m/e 381 ($M^+$).

Example 17d 1-(3-Chloro-4-methanesulfonyl-thiophen-2-yl)-2-(6-methyl-2-p-tolyl-imidazo[1,2-a]pyridin-3-yl)-ethanone

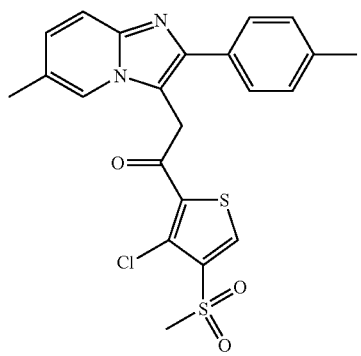

Prepared from the decarboxylation of the methyl ester obtained by the reaction of (6-methyl-2-p-tolyl imidazo[1,2-a]pyridin-3-yl)acetic acid methyl ester 35a and 3-chloro-4-methanesulfonyl-thiophen-2-carbonyl chloride using a procedure similar to that described in Example 13. $^1$H NMR (400 MHz, $CDCl_3$) δ 2.34 (s, 3H), 2.39 (s, 3H), 3.25 (s, 3H), 4.76 (s, 2H), 7.11 (d, J=8.8 Hz, 1H), 7.25 (d, J=8.0 Hz, 2H), 7.51

(d, J=8.0 Hz, 2H), 7.56 (s, 1H), 7.62 (d, J=9.1 Hz, 1H), 8.49 (s, 1H). Mass spectrum m/e 459 (M+).

Example 18d 1-(1,5-Dimethyl-1H-[1,2,3]triazol-4-yl)-2-(6-methyl-2-p-tolyl-imidazo[1,2-a]pyridin-3-yl)-ethanone

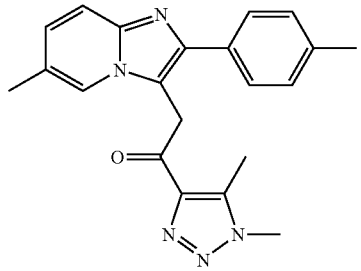

Prepared from the decarboxylation of the methyl ester obtained by the reaction of (6-methyl-2-p-tolyl imidazo[1,2-a]pyridin-3-yl)acetic acid methyl ester 35a and 1,5-dimethyl-1H-[1,2,3]triazol-4-carbonyl chloride using a procedure similar to that described in Example 13. $^1$H NMR (400 MHz, CDCl$_3$) δ 2.32 (s, 3H), 2.37 (s, 3H), 2.59 (s, 3H), 4.03 (s, 3H), 4.92 (s, 2H), 7.10 (dd, J=1.6, 12.0 Hz, 1H), 7.24 (m, 2H), 7.65 (m, 3H), 7.77 (s, 1H). Mass spectrum m/e 360 (M+).

Example 19d

1-[1-(6-Methyl-pyridin-2-yl)-1H-imidazol-4-yl]-2-(6-methyl-2-p-tolyl-imidazo[1,2-a]pyridin-3-yl)-ethanone

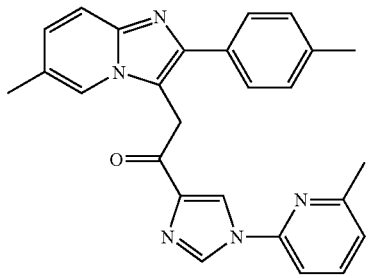

Prepared from the decarboxylation of the methyl ester obtained by the reaction of (6-methyl-2-p-tolyl imidazo[1,2-a]pyridin-3-yl)acetic acid methyl ester 35a and 1-(6-methyl-pyridin-2-yl)-1H-imidazol-4-carbonyl chloride using a procedure similar to that described in Example 13. $^1$H NMR (400 MHz, CDCl$_3$) δ 2.23 (s, 3H), 2.32 (s, 3H), 2.51 (s, 3H), 4.75 (s, 2H), 6.97 (dd, J=1.1, 9.1 Hz, 1H), 7.08 (dd, J=5.8, 7.7 Hz, 2H), 7.18 (d, J=8.0 Hz, 2H), 7.49 (d, J=9.1 Hz, 1H), 7.61 (m, 3H), 7.74 (s, 1H), 8.29 (s, 1H), 8.39 (s, 1H). Mass spectrum m/e 422 (M+).

Example 20d 1-(2,7-Dimethyl-imidazo[1,2-a]pyridin-3-yl)-2-(6-methyl-2-p-tolyl-imidazo[1,2-a]pyridin-3-yl)-ethanone

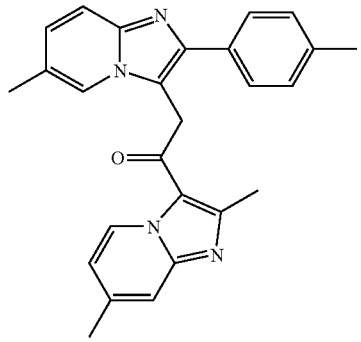

Prepared from the decarboxylation of the methyl ester obtained by the reaction of (6-methyl-2-p-tolyl imidazo[1,2-a]pyridin-3-yl)acetic acid methyl ester 35a and 2,7-dimethyl-imidazo[1,2-a]pyridin-3-carbonyl chloride using a procedure similar to that described in Example 13. $^1$H NMR (400 MHz, CDCl$_3$) δ 2.31 (s, 3H), 2.41 (s, 3H), 2.47 (s, 3H), 2.84 (s, 3H), 4.59 (s, 2H), 6.55 (d, J=6.6 Hz, 1H), 6.87 (d, J=6.9 Hz, 1H), 7.06 (d, J=9.1 Hz, 1H), 7.22 (m, 2H), 7.56 (m, 2H), 7.67 (s, 1H), 7.88 (d, J3=6.9 Hz, 1H), 9.58 (d, J=1H). Mass spectrum m/e 409 (Me.

Example 21d 1-(3,5-Dimethyl-1-phenyl-1H-pyrazol-4-yl)-2-(6-methyl-2-p-tolyl-imidazo[1,2-a]pyridin-3-yl)-ethanone

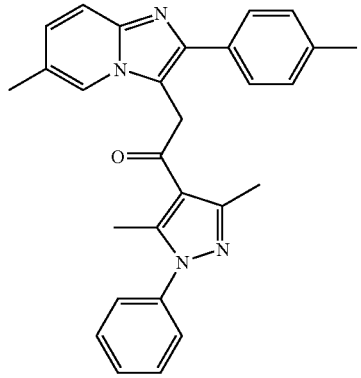

Prepared from the decarboxylation of the methyl ester obtained by the reaction of (6-methyl-2-p-tolyl imidazo[1,2-a]pyridin-3-yl)acetic acid methyl ester 35a and 3,5-dimethyl-1-phenyl-1H-pyrazol-4-carbonyl chloride using a procedure similar to that described in Example 13. $^1$H NMR (400 MHz, CDCl$_3$) δ 2.33 (s, 3H), 2.38 (s, 3H), 2.54 (s, 3H), 2.61 (s, 3H), 4.50 (s, 2H), 7.08 (m, 2H), 7.25 (m, 2H), 7.50 (m, 8H). Mass spectrum m/e 435 (M+).

Example 22D 1-(3-Methoxy-thiophen-2-yl)-2-(6-methyl-2-p-tolyl-imidazo[1,2-a]pyridin-3-yl)-ethanone

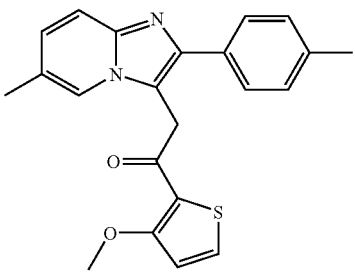

Prepared from the decarboxylation of the methyl ester obtained by the reaction of (6-methyl-2-p-tolyl imidazo[1,2-a]pyridin-3-yl)acetic acid methyl ester 35a and 3-methoxy-thiophen-2-carbonyl chloride using a procedure similar to that described in Example 13. $^1$H NMR (400 MHz, CDCl$_3$) δ 2.31 (s, 3H), 2.38 (s, 3H), 3.95 (s, 3H), 4.63 (s, 2H), 6.87 (dd, J=0.8, 7.2 Hz, 1H), 6.93 (dd, J=0.8, 7.2 Hz, 1H), 7.03 (dd, J=2.4, 12.4 Hz, 2H), 7.23 (d, J=10.4 Hz, 2H), 7.62 (m, 3H). Mass spectrum m/e 377 (M$^+$).

Example 23d 1-(2-Methyl-imidazo[1,2-a]pyridin-3-yl)-2-(6-methyl-2-p-tolyl-imidazo[1,2-a]pyridin-3-yl)-ethanone

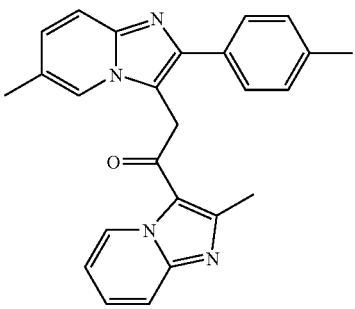

Prepared from the decarboxylation of the methyl ester obtained by the reaction of (6-methyl-2-p-tolyl imidazo[1,2-a]pyridin-3-yl)acetic acid methyl ester 35a and 2-methyl-imidazo[1,2-a]pyridin-3-carbonyl chloride using a procedure similar to that described in Example 13. $^1$H NMR (400 MHz, CDCl$_3$) δ 2.34 (s, 3H), 2.36 (s, 3H), 2.88 (s, 3H), 4.63 (s, 2H), 7.05 (t, J=8.0 Hz, 1H), 7.12 (d, J=10.2 Hz, 1H), 7.22 (d, J=7.7 Hz, 2H), 7.55 (m, 3H), 7.70 (m, 3H), 9.74 (d, J=7.0 Hz, 1H). Mass spectrum m/e 395 (M$^+$).

Example 24d 1-(5-Methyl-thiophen-2-yl)-2-(6-methyl-2-p-tolyl-imidazo[1,2-a]pyridin-3-yl)-ethanone

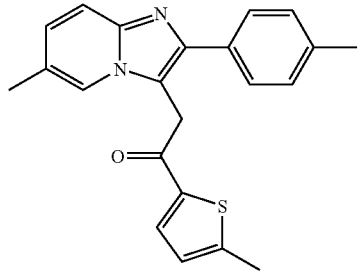

Prepared from the decarboxylation of the methyl ester obtained by the reaction of (6-methyl-2-p-tolyl imidazo[1,2-a]pyridin-3-yl)acetic acid methyl ester 35a and 5-methyl-thiophen-2-carbonyl chloride using a procedure similar to that described in Example 13. $^1$H NMR (400 MHz, CDCl$_3$) δ 2.24 (s, 3H), 2.35 (s, 3H), 2.46 (s, 3H), 4.47 (s, 2H), 6.70 (d, J3=3.7 Hz, 1H), 6.97 (dd, J=1.4, 9.1 Hz, 1H), 7.21 (d, J=7.7 Hz, 2H), 7.42 (d, J=3.7 Hz, 1H), 7.49 (d, J=9.1 Hz, 1H), 7.54 (d, J=7.7 Hz, 2H), 7.71 (s, 1H). Mass spectrum m/e 361 (M$^+$).

Example 25d 1-(3-Methyl-thiophen-2-yl)-2-(6-methyl-2-p-tolyl-imidazo[1,2-a]pyridin-3-yl)-ethanone

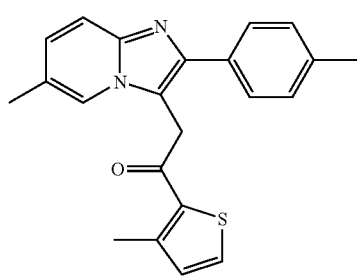

Prepared from the decarboxylation of the methyl ester obtained by the reaction of (6-methyl-2-p-tolyl imidazo[1,2-a]pyridin-3-yl)acetic acid methyl ester 35a and 3-methyl-thiophen-2-carbonyl chloride using a procedure similar to that described in Example 13. $^1$H NMR (400 MHz, CDCl$_3$) δ 2.31 (s, 3H), 2.38 (s, 3H), 2.59 (s, 3H), 4.56 (s, 2H), 7.00 (d, J3=5.1 Hz, 1H), 7.04 (d, J=9.5 Hz, 1H), 7.23 (d, J=8.0 Hz, 2H), 7.45 (d, J=5.1 Hz, 1H), 7.57 (m, 3H), 7.68 (s, 1H). Mass spectrum m/e 361 (M$^+$).

Example 26d 1-(1,5-Dimethyl-1H-pyrazol-3-yl)-2-(6-methyl-2-p-tolyl-imidazo[1,2-a]pyridin-3-yl)-ethanone

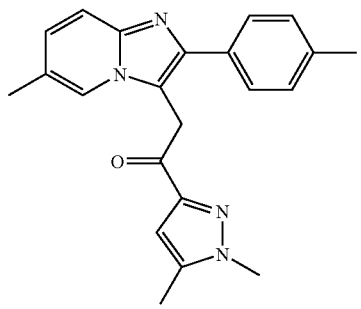

Prepared from the decarboxylation of the methyl ester obtained by the reaction of (6-methyl-2-p-tolyl imidazo[1,2-a]pyridin-3-yl)acetic acid methyl ester 35a and 1,5-dimethyl-1H-pyrazol-3-carbonyl chloride using a procedure similar to that described in Example 13. $^1$H NMR (400 MHz, CDCl$_3$) δ 2.21 (s, 3H), 2.31 (s, 3H), 2.38 (s, 3H), 4.06 (s, 3H), 4.47 (s, 2H), 6.48 (s, 1H), 7.03 (d, J=9.1 Hz, 1H), 7.24 (d, J=8.0 Hz, 2H), 7.50 (d, J=8.0 Hz, 2H), 7.54 (d, J=9.1 Hz, 1H), 7.69 (s, 1H). Mass spectrum m/e 359 (M$^+$).

Example 27d 1-(2,5-Dimethyl-1H-pyrazol-3-yl)-2-(6-methyl-2-p-tolyl-imidazo[1,2-a]pyridin-3-yl)-ethanone

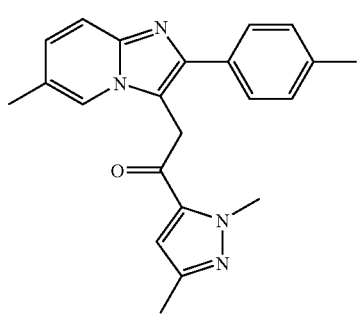

Prepared from the decarboxylation of the methyl ester obtained by the reaction of (6-methyl-2-p-tolyl imidazo[1,2-a]pyridin-3-yl)acetic acid methyl ester 35a and 2,5-dimethyl-1H-pyrazol-3-carbonyl chloride using a procedure similar to that described in Example 13. $^1$H NMR (400 MHz, CDCl$_3$) δ 2.21 (s, 3H), 2.31 (s, 3H), 2.38 (s, 3H), 4.06 (s, 3H), 4.47 (s, 2H), 6.48 (s, 1H), 7.03 (d, J=9.1 Hz, 1H), 7.24 (d, J=8.0 Hz, 2H), 7.50 (d, J3=8.0 Hz, 2H), 7.54 (d, J=9.1 Hz, 1H), 7.69 (s, 1H). Mass spectrum m/e 359 (M$^+$).

Example 28d 1-(1-Methyl-1H-imidazol-4-yl)-2-(6-methyl-2-p-tolyl-imidazo[1,2-a]pyridin-3-yl)-ethanone

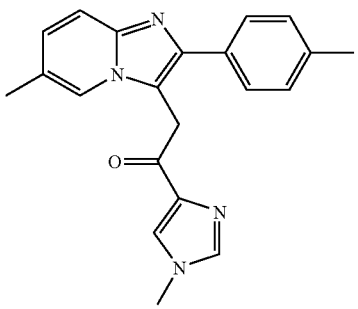

Prepared from the decarboxylation of the methyl ester obtained by the reaction of (6-methyl-2-p-tolyl imidazo[1,2-a]pyridin-3-yl)acetic acid methyl ester 35a and 1-methyl-1H-imidazol-4-carbonyl chloride using a procedure similar to that described in Example 13. $^1$H NMR (400 MHz, CDCl$_3$) δ 2.28 (s, 3H), 2.36 (s, 3H), 3.71 (s, 3H), 4.72 (s, 2H), 7.02 (dd, J=1.4, 9.1 Hz, 1H), 7.21 (d, J=7.7 Hz, 2H), 7.48 (s, 1H), 7.55 (m, 2H), 7.65 (d, J=7.7 Hz, 2H), 7.76 (s, 1H). Mass spectrum m/e 345 (M$^+$).

Example 29d 1-(5,7-Dimethyl-pyrazolo[1,5-a]pyrimidin-3-yl)-2-(6-methyl-2-p-tolyl-imidazo[1,2-a]pyridin-3-yl)-ethanone

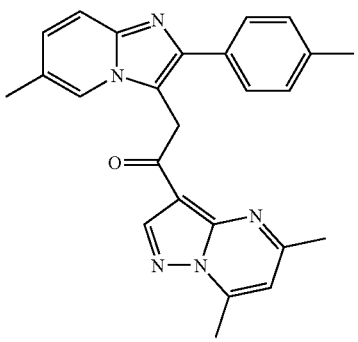

Prepared from the decarboxylation of the methyl ester obtained by the reaction of (6-methyl-2-p-tolyl imidazo[1,2-a]pyridin-3-yl)acetic acid methyl ester 35a and 5,7-dimethyl-pyrazolo[1,5-a]pyrimidin-3-carbonyl chloride using a procedure similar to that described in Example 13. $^1$H NMR (400 MHz, CDCl$_3$) δ 2.25 (s, 3H), 2.33 (s, 3H), 2.58 (s, 3H), 2.77 (s, 3H), 4.98 (s, 2H), 6.76 (s, 1H), 7.01 (d, J=9.1 Hz, 1H), 7.16 (d, J=7.7 Hz, 2H), 7.54 (d, J=9.1 Hz, 1H), 7.63 (d, J=7.7 Hz, 2H), 7.74 (s, 1H), 8.59 (s, 1H). Mass spectrum m/e 410 (M$^+$).

Example 30d 1-(1-Methyl-1H-pyrrol-2-yl)-2-(6-methyl-2-p-tolyl-imidazo[1,2-a]pyridin-3-yl)-ethanone

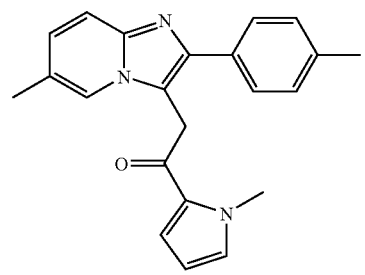

Prepared from the decarboxylation of the methyl ester obtained by the reaction of (6-methyl-2-p-tolyl imidazo[1,2-a]pyridin-3-yl)acetic acid methyl ester 35a and 1-methyl-1H-pyrrol-2-carbonyl chloride using a procedure similar to that described in Example 13. $^1$H NMR (400 MHz, CDCl$_3$) δ 2.32 (s, 3H), 2.39 (s, 3H), 3.94 (s, 3H), 4.52 (s, 2H), 6.15 (dd, J=2.5, 4.0 Hz, 1H), 6.88 (s, 1H), 7.03 (m, 2H), 7.23 (d, J=8.0 Hz, 2H), 7.54 (d, J=9.1 Hz, 1H), 7.59 (d, J=8.0 Hz, 2H), 7.79 (s, 1H). Mass spectrum m/e 344 (M$^+$).

Example 31d

2-[2-(4-Methoxy-phenyl)-6-methyl-imidazo[1,2-a]pyridin-3-yl]-1-(1-methyl-1H-pyrrol-2-yl)-ethanone

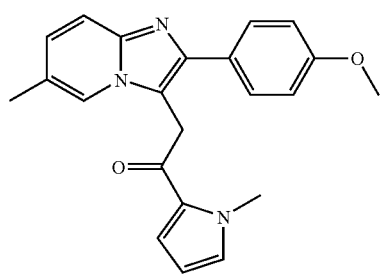

Prepared from the decarboxylation of the ethyl ester obtained by the reaction of [2-(4-methoxy-phenyl)-6-methyl-imidazo[1,2-a]pyridin-3-yl]-acetic acid ethyl ester and 1-methyl-1H-pyrrol-2-carbonyl chloride using a procedure similar to that described in Example 13. $^1$H NMR (400 MHz, CDCl$_3$) δ 2.40 (s, 3H), 3.84 (s, 3H), 3.95 (s, 3H), 4.53 (s, 2H), 6.20 (dd, J=2.5, 4.4 Hz, 1H), 6.94 (s, 1H), 7.00 (d, J=8.4 Hz, 2H), 7.07 (dd, J=1.4, 4.4 Hz, 1H), 7.33 (d, J=8.8 Hz, 1H), 7.68 (d, J=8.4 Hz, 2H), 7.91 (s, 1H), 8.00 (d, J=8.8 Hz, 1H). Mass spectrum m/e 360 (M$^+$).

Example 32d 1-(3,5-Dimethyl-isoxazol-4-yl)-2-(6-methyl-2-p-tolyl-imidazo[1,2-a]pyridin-3-yl)-ethanone

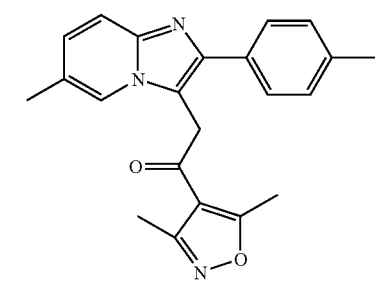

Prepared from the decarboxylation of the methyl ester obtained by the reaction of (6-methyl-2-p-tolyl imidazo[1,2-a]pyridin-3-yl)acetic acid methyl ester 35a and 3,5-dimethyl-isoxazol-4-carbonyl chloride using a procedure similar to that described in Example 13. $^1$H NMR (400 MHz, CDCl$_3$) δ 2.34 (s, 3H), 2.38 (s, 3H), 2.49 (s, 3H), 2.69 (s, 3H), 4.41 (s, 2H), 7.07 (dd, J=1.1, 9.5 Hz, 1H), 7.24 (d, J=8.0 Hz, 2H), 7.47 (d, J=8.0 Hz, 2H), 7.57 (m, 2H). Mass spectrum m/e 360 (M$^+$).

Example 33d 2-(6-Methyl-2-p-tolyl-imidazo[1,2-a]pyridin-3-yl)-1-thiazol-2-yl-ethanone

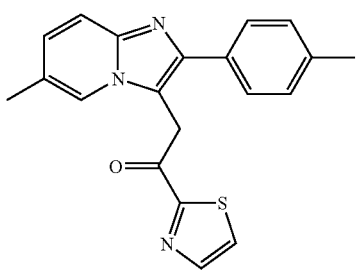

Prepared from the decarboxylation of the methyl ester obtained by the reaction of (6-methyl-2-p-tolyl imidazo[1,2-a]pyridin-3-yl)acetic acid methyl ester 35a and 1-thiazol-2-carbonyl chloride using a procedure similar to that described in Example 13. $^1$H NMR (400 MHz, CDCl$_3$) δ 2.31 (s, 3H), 2.38 (s, 3H), 4.94 (s, 2H), 7.05 (dd, J=1.5, 9.1 Hz, 1H), 7.23 (d, J=8.0 Hz, 2H), 7.56 (d, J=9.1 Hz, 1H), 7.64 (d, J=8.0 Hz, 2H), 7.74 (s, 1H), 7.78 (d, J=2.9 Hz, 1H), 8.08 (d, J=2.9 Hz, 1H). Mass spectrum m/e 348 (M$^+$).

Example 34d 2-(6-Methyl-2-p-tolyl-imidazo[1,2-a]pyridin-3-yl)-1-(1,2,5-trimethyl-1H-pyrrol-3-yl)-ethanone

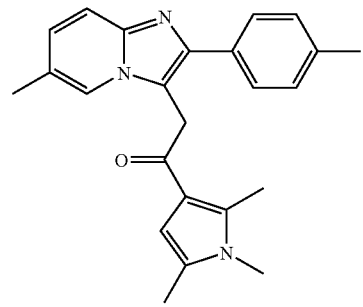

Prepared from the decarboxylation of the methyl ester obtained by the reaction of (6-methyl-2-p-tolyl imidazo[1,2-a]pyridin-3-yl)acetic acid methyl ester 35a and 1,2,5-trimethyl-1H-pyrrol-3-carbonyl chloride using a procedure similar to that described in Example 13. $^1$H NMR (400 MHz, CDCl$_3$) δ 2.18 (s, 3H), 2.32 (s, 3H), 2.38 (s, 3H), 2.62 (s, 3H), 3.41 (s, 3H), 4.42 (s, 2H), 6.20 (s, 1H), 7.07 (d, J=9.1 Hz, 1H), 7.23 (d, J=7.7 Hz, 2H), 7.59 (d, J=7.7 Hz, 2H), 7.63 (d, J=9.1 Hz, 1H), 7.79 (s, 1H). Mass spectrum m/e 372 (M$^+$).

The following compounds were also synthesized according to Method C, and in vitro data for these compounds are shown in Tables 1a or Table 1b.

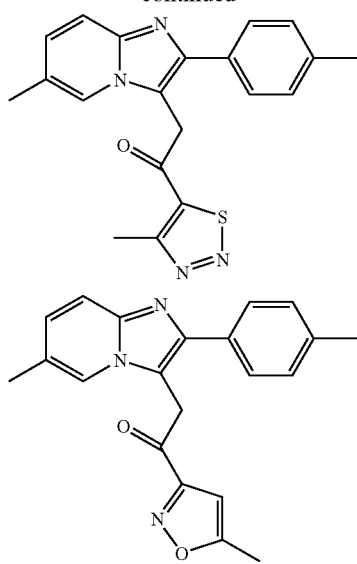

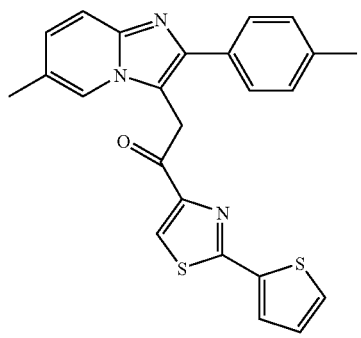

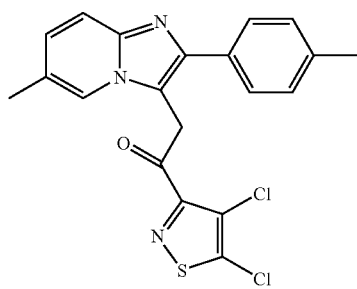

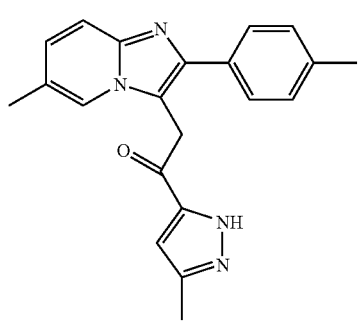

Method D (for the Synthesis of Lactams)

-continued

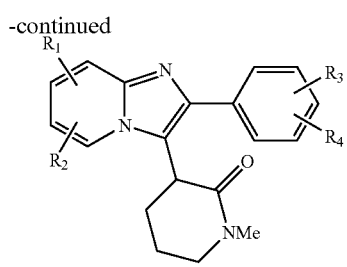

From Method D

Example 35a (6-Methyl-2-p-tolyl-imidazo[1,2-a]pyridin-3-yl)-acetic acid methyl ester

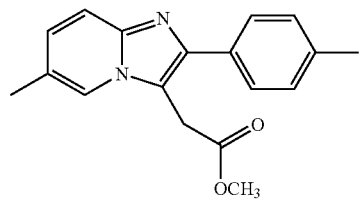

To a magnetically stirred solution of (6-methyl-2-p-tolyl-imidazo[1,2-a]pyridin-3-yl)-acetic acid 1a (5.0 g, 17.85 mmol) in methanol (MeOH) (25 mL) at 0° C. under Ar atmosphere was slowly added SOCl$_2$ (2.60 mL, 35.7 mmol). The reaction mixture was stirred for 2 h and then concentrated in vacuo. Aqueous 10% Na$_2$CO$_3$ solution (100 mL) was added, and the aqueous phase was extracted with EtOAc (2×200 mL). The combined organic layers were washed with aqueous NaHCO$_3$ solution, dried (MgSO$_4$), and concentrated in vacuo to the provide the title compound (4.2 g, 80%) as yellow solids. $^1$H NMR (400 MHz, CDCl$_3$) δ 2.37 (s, 3H), 2.40 (s, 3H), 3.76 (s, 3H), 4.03 (s, 2H), 7.07 (dd, J=1.7, 9.1 Hz, 1H), 7.28 (d, J=8.3 Hz, 2H), 7.55 (d, J=9.1 Hz, 1H), 7.70 (dd, J=1.8, 6.3 Hz, 2H), 7.85 (s, 1H). $^{13}$C-NMR (100 MHz, CDCl$_3$) δ 18.7, 21.5, 30.8, 52.7, 112.4, 117.0, 121.5, 122.2, 127.8, 128.5, 129.6, 131.6, 137.7, 144.2, 144.6, 170.3.

Example 35b (+/−)-4-[1,3]Dioxolan-2-yl-2-(6-methyl-2-p-tolyl-imidazo[1,2-a]pyridin-3-yl)-butyric acid methyl ester

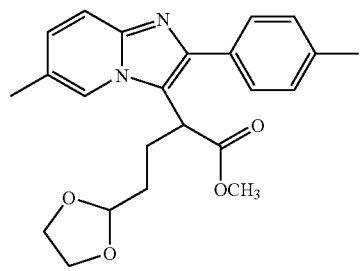

To a magnetically stirred solution of diisopropyl amine (1.76 mL, 12.6 mmol) in THF (10.0 mL) at 0° C. under Ar atmosphere was added n-butyllithium (7.35 mL, 1.6M, 11.76 mmol) forming lithium diisopropylamide (LDA). The reaction mixture was stirred for 15 min at 0° C., then a THF solution of (6-methyl-2-p-tolyl-imidazo[1,2-a]pyridin-3-yl)-acetic acid methyl ester 35a (2.47 g, 8.40 mmol) was added. After an additional 15 min at 0° C., 2-(2-bromoethyl)-1,3-dioxolane (2.48 mL, 16.8 mmol) was added. The reaction mixture was stirred for 24 h at room temperature. The crude reaction was concentrated in vacuo. Water (100 mL) was added, and the aqueous phase was extracted with ethyl acetate (2×100 mL). The combined organic layers were washed with water, dried (MgSO$_4$), and concentrated in vacuo to the crude product. The pure product was obtained by column chromatography over silica gel (20:80 EtOAc/hexanes, then 40:60 EtOAc/hexanes as eluent) which gave the title compound (0.52 g, 16%) as a white solid. $^1$H NMR (400 MHz, CDCl$_3$) δ 1.41 (m, 1H), 1.50 (m, 1H), 2.03 (m, 2H), 2.33 (s, 3H), 2.40 (s, 3H), 3.70 (s, 3H), 3.76 (m, 4H), 4.45 (td, J=2.2, 7.7 Hz, 1H), 4.71 (m, 1H), 7.02 (d, J=9.1 Hz, 1H), 7.25 (d, J=2.2 Hz, 2H), 7.51 (d, J=9.1 Hz, 1H), 7.60 (d, J=2.2 Hz, 2H), 8.05 (s, 1H).

Example 35c (+/−)-2-(6-Methyl-2-p-tolyl-imidazo[1,2-a]pyridin-3-yl)-5-oxo-pentanoic acid methyl ester

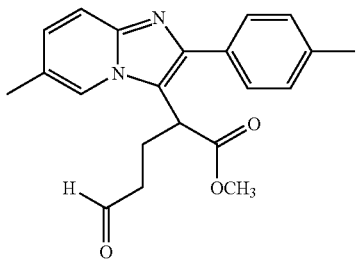

To a magnetically stirred solution of (+/−)-4-[1,3]dioxolan-2-yl-2-(6-methyl-2-p-tolyl-imidazo[1,2-a]pyridin-3-yl)-butyric acid methyl ester 35b (0.10 g, 0.253 mmol) in acetone (5 mL) at room temperature under Ar atmosphere was slowly added 5N HCl (1.5 mL). The reaction mixture was stirred for 2 h and then concentrated to remove acetone. NaHCO$_3$ solution (100 mL) was added until the pH is greater than 9, and the aqueous phase was extracted with ethyl acetate (2×100 mL). The combined organic layers were washed with water, dried (MgSO$_4$), and concentrated in vacuo to the crude product. $^1$H NMR (400 MHz, CDCl$_3$) δ 2.24 (m, 4H), 2.34 (s, 3H), 2.39 (s, 3H), 3.70 (s, 3H), 4.38 (t, J=8.1 Hz, 1H), 7.03 (d, J=1.4 Hz, 1H), 7.24 (d, J=7.3 Hz, 2H), 7.56 (m, 3H), 7.99 (s, 1H), 9.48 (s, 1H).

Example 35d (+/−)-1-Methyl-3-(6-methyl-2-p-tolyl-imidazo[1,2-a]pyridin-3-yl)-piperidin-2-one

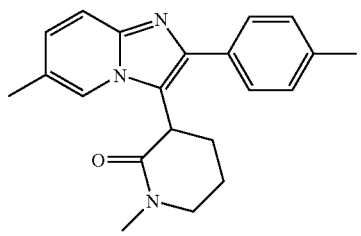

To a magnetically stirred solution of (+/−)-2-(6-methyl-2-p-tolyl-imidazo[1,2-a]pyridin-3-yl)-5-oxo-pentanoic acid methyl ester 35c (0.085 g, 0.253 mmol) in methanol (1 mL) at room temperature under Ar atmosphere was added a 40% aqueous solution of methyl amine (MeNH$_2$) (0.021 mL, 0.253 mmol). The reaction mixture was stirred for 1 h at room temperature. NaBH$_4$ (0.019 g, 0.506 mmol) was added at room temperature. After 30 min, water (30 mL) was added, and the aqueous phase was extracted with EtOAc (2×50 mL). The combined organic layers were dried (MgSO$_4$), and concentrated in vacuo to the crude product. The pure product was obtained by column chromatography over silica gel (EtOAc, then 4:96 MeOH/EtOAc as eluent) which gave the title compound (0.03 g, 31%) as a white solid. The combined organic layers were washed with water, dried (MgSO$_4$), and concentrated in vacuo to the crude product. $^1$H NMR (400 MHz, CDCl$_3$) δ 1.99 (m, 3H), 2.11 (m, 1H), 2.31 (s, 3H), 2.38 (s, 3H), 3.05 (s, 3H), 3.41 (m, 1H), 3.53 (m, 1H), 4.25 (m, 1H), 6.99 (d, J=9.1 Hz, 1H), 7.22 (m, 3H), 7.46 (s, 1H), 7.53 (m, 2H). $^{13}$C NMR (100 MHz, CDCl$_3$) δ 18.9, 21.5, 23.1, 26.1, 35.4, 39.7, 50.3, 117.4, 119.1, 121.5, 121.7, 127.0, 129.1, 129.3, 132.4, 137.5, 143.9, 144.4, 168.7. Mass spectrum m/e 335 (M$^+$).

Example 35e (+)-1-Methyl-3-(6-methyl-2-p-tolyl-imidazo[1,2-a]pyridin-3-yl)-piperidin-2-one

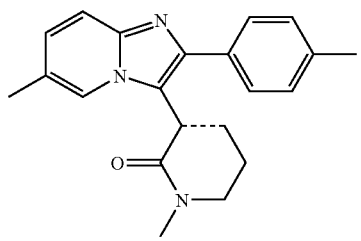

The (+)-isomer was separated from the (−)-isomer by semi-prep HPLC (Chiralpak AD, mobile phase 90% hexane/10% EtOH, 6 mL/min). The (+)-isomer elutes at approximately 16.3 min. (−)-isomer elutes at approximately 13.42 min. This separation yielded 20 mg of the (+)-isomer and 20 mg of the (−)-isomer. However, the absolute stereochemistry is not known. The optical purity is 99.84% ee. [α]=+23.9° (c. 0.33, CH$_2$Cl$_2$). $^1$H NMR (400 MHz, CDCl$_3$) δ 1.99 (m, 3H), 2.11 (m, 1H), 2.31 (s, 3H), 2.38 (s, 3H), 3.05 (s, 3H), 3.41 (m, 1H), 3.53 (m, 1H), 4.25 (m, 1H), 6.99 (d, J=9.1 Hz, 1H), 7.22 (m, 3H), 7.46 (s, 1H), 7.53 (m, 2H). Mass spectrum (m/e) 335 (M$^+$).

Example 35f (−)-1-Methyl-3-(6-methyl-2-p-tolyl-imidazo[1,2-a]pyridin-3-yl)-piperidin-2-one

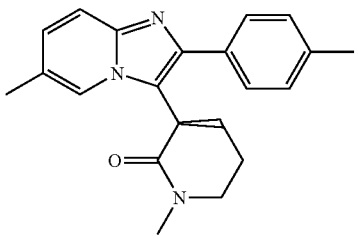

The optical purity is 100% ee. [α]=−24.52° (c. 0.52, CH$_2$Cl$_2$). Mass spectrum (m/e) 335 (M$^+$). $^1$H NMR spectrum is identical to the (+)-enantiomer.

Example 36a (+/−)-2-(6-Methyl-2-p-tolyl-imidazo[1,2-a]pyridin-3-yl)-pent-4-enoic acid methyl ester

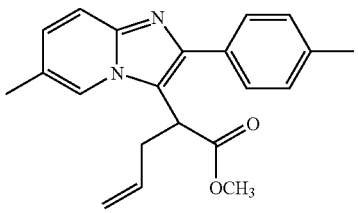

To a magnetically stirred solution of diisopropyl amine (0.88 mL, 8.16 mmol) in THF (12.0 mL) at 0° C. under Ar atmosphere was added n-butyllithium (3.62 mL, 1.6M, 7.48 mmol). The reaction mixture was stirred for 15 min at 0° C., then a THF solution of (6-methyl-2-p-tolyl-imidazo[1,2-a]pyridin-3-yl)-acetic acid methyl ester 35a (1.55 g, 5.27 mmol) was added. After an additional 15 min at 0° C., allyl bromide (0.60 mL, 8.84 mmol) was added. The reaction mixture was stirred for 18 h at room temperature. The crude reaction was concentrated in vacuo. Water (100 mL) was added, and the aqueous phase was extracted with ethyl acetate (2×100 mL). The combined organic layers were washed with water, dried (MgSO$_4$), and concentrated in vacuo to the crude product. The pure product was obtained by column chromatography over silica gel (15:85 EtOAc/hexanes, then 50:50 EtOAc/hexanes as eluent), which gave the title compound (0.52 g, 32%) as a white solid. $^1$H NMR (400 MHz, CDCl$_3$) δ 2.35 (s, 3H), 2.40 (s, 3H), 2.64 (m, 1H), 3.00 (m, 1H), 3.70 (s, 3H), 4.43 (t, J=8.0 Hz, 1H), 4.90 (d, J=10.2 Hz, 1H), 4.94

(d, J=16.8 Hz, 1H), 5.56 (m, 1H), 7.03 (d, J=9.1 Hz, 1H), 7.26 (d, J=7.7 Hz, 2H), 7.53 (d, J=9.1 Hz, 1H), 7.62 (d, J=7.7 Hz, 2H), 8.09 (s, 1H).

Example 36b 2-(6-Methyl-2-p-tolyl-imidazo[1,2-a]pyridin-3-yl)-4-oxo-butyric acid methyl ester

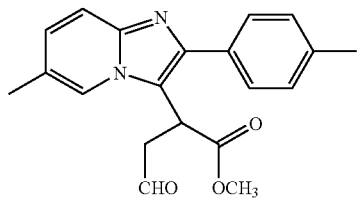

To a magnetically stirred solution of (+/−)-2-(6-methyl-2-p-tolyl-imidazo[1,2-a]pyridin-3-yl)-pent-4-enoic acid methyl ester 36a (0.10 g, 0.299 mmol) in water (3 mL) and THF (1 mL) at room temperature under Ar atmosphere were slowly added OsO$_4$ (3 uL, 0.003 mmol) and NaIO$_4$ (0.16 g). The reaction mixture was stirred for 3 h at room temperature. Water (100 mL) was added, and the aqueous phase was extracted with ethyl acetate (2×100 mL). The combined organic layers were washed with water, dried (NgSO$_4$), and concentrated in vacuo to the crude product. The pure product was obtained by column chromatography over silica gel (20:80 EtOAc/hexanes, then 50:50 EtOAc/hexanes as eluent) which gave the title compound (0.015 g, 14%) as a white solid. $^1$H NMR (400 MHz, CDCl$_3$) δ 2.36 (s, 3H), 2.40 (s, 3H), 2.64 (dd, J=4.0, 18.7 Hz, 1H), 3.71 (s, 3H), 3.72 (dd, J=10.2, 18.7 Hz, 1H), 4.96 (dd, J=4.0, 10.2 Hz, 1H), 7.07 (dd, J=1.4, 9.1 Hz, 1H), 7.28 (d, J=7.7 Hz, 2H), 7.55 (d, J=9.1 Hz, 1H), 7.60 (d, J=2H), 7.95 (s, 1H), 9.73 (s, 1H).

Example 36c (+/−)-1-Methyl-3-(6-methyl-2-p-tolyl-imidazo[1,2-a]pyridin-3-yl)-pyrrolidin-2-one

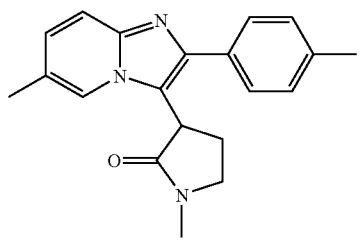

To a magnetically stirred solution of 2-(6-methyl-2-p-tolyl-imidazo[1,2-a]pyridin-3-yl)-4-oxo-butyric acid methyl ester 36b (0.035 g, 0.0988 mmol) in methanol (1 mL) at room temperature under Ar atmosphere was added a 40% aqueous solution of methyl amine (0.009 mL, 0.0988 mmol). The reaction mixture was stirred for 1 h at room temperature. NaBH$_4$ (0.0074 g, 0.197 mmol) was added at room temperature. After 30 min, water (30 mL) was added, and the aqueous phase was extracted with EtOAc (2×50 mL). The combined organic layers were dried (MgSO$_4$), and concentrated in vacuo to the crude product. The pure product was obtained by column chromatography over silica gel (EtOAc, then 4:96 MeOH/EtOAc as eluent), which gave the title compound (0.006 g, 19%) as a white solid. (400 MHz, CDCl$_3$) δ2.31 (s, 3H), 2.33 (m, 2H), 2.39 (s, 3H), 3.00 (s, 3H), 3.51 (m, 2H), 4.41 (t, J=10.2 Hz, 1H), 7.02 (dd, J=1.1, 9.1 Hz, 1H), 7.24 (d, J=7.7 Hz, 2H), 7.25 (s, 1H), 7.53 (m, 3H).

ADDITIONAL EXAMPLES

Example 37

From Method B 2-(6-Methyl-2-p-tolyl-imidazo[1,2-a]pyridin-3-yl)-1-(1,3,5-trimethyl-1H-pyrazol-4-yl)-ethanone

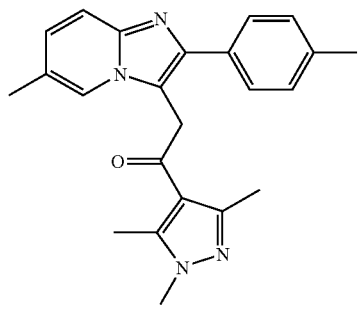

Prepared from (6-methyl-2-p-tolyl-imidazo[1,2-a]pyridine-3-yl)-acetaldehyde 6b and 4-bromo-1,3,5-trimethyl-1H-pyrazole using the procedure of Method B described above. $^1$H NMR (400 MHz, CDCl$_3$) δ2.33 (s, 3H), 2.38 (s, 3H), 2.52 (s, 3H), 2.53 (s, 3H), 3.78 (s, 3H), 4.43 (s, 2H), 7.04 (d, J=8.8 Hz, 1H), 7.22 (m, 3H), 7.57 (m, 3H). Mass spectrum (m/e) 373 (M$^+$).

Example 38

From Method C 1-(3-Methyl-3H-imidazol-4-yl)-2-(6-methyl-2-p-tolyl-imidazo[1,2-a]pyridine-3-yl)-ethanone

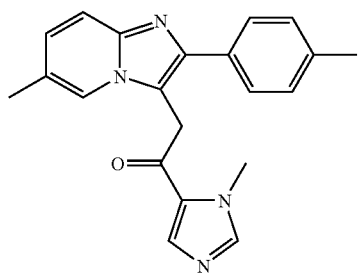

Prepared from (6-methyl-2-p-tolyl-imidazo[1,2-a]pyridin-3-yl)-acetic acid methyl ester 35a and 3-methyl-3H-imidazole-4-carbonyl chloride using the procedure of Method C described above. $^1$H NMR (400 MHz, CDCl$_3$) δ2.34 (s, 3H), 2.39 (s, 3H), 3.91 (s, 3H), 4.52 (s, 2H), 7.05 (dd, J=1.1, 9.1 Hz, 1H), 7.26 (m, 2H), 7.57 (m, 4H), 7.74 (s, 1H), 7.80 (s, 1H). Mass spectrum (m/e) 345 (M+).

Example 39

From Method C

1-Benzo[b]thiophen-2-yl-2-(6-methyl-2-p-tolyl-imidazo[1,2-a]pyridin-3-yl)-ethanone

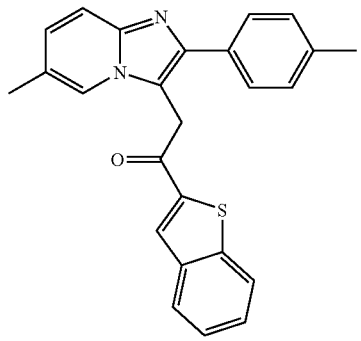

Prepared from (6-methyl-2-p-tolyl-imidazo[1,2-a]pyridin-3-yl)-acetic acid methyl ester 35a and benzo[b]thiophene-2-carbonyl chloride using the procedure of Method C described above. $^1$H NMR (400 MHz, CDCl$_3$) δ2.31 (s, 3H), 2.42 (s, 3H), 4.68 (s, 2H), 7.04 (d, J=9.1 Hz, 1H), 7.29 (d, J=7.7 Hz, 2H), 7.37 (t, J=7.7 Hz, 1H), 7.44 (5.8 Hz, 1H), 7.56 (m, 3H), 7.70 (m, 2H), 7.83 (m, 2H). Mass spectrum (m/e) 397 (M+).

Example 40

From Method C 1-(2,3-Dihydro-benzo[1,4]dioxin-2-yl)-2-(6-methyl-2-p-tolyl-imidazo[1,2-a]pyridin-3-yl)-ethanone

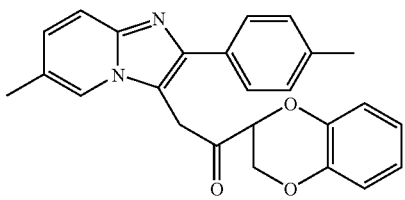

(6-Methyl-2-p-tolyl-imidazo[1,2,a]pyridin-3-yl)-acetic acid methyl ester 35a (447 mg, 1.5 mmol) was dissolved in anhydrous THF (15 mL) and cooled to −78° C. Potassium hexamethyldisilazide (0.5M in toluene, 3.0 mL, 1.5 mmol) was added slowly and the resulting bright orange solution was stirred at −78° C. for 10 minutes. 2,3-Dihydro-benzo[1,4]dioxine-2-carbonyl chloride (150 mg, 0.76 mmol) dissolved in anhydrous THF (10 mL) was added dropwise to the enolate solution. The resulting yellow solution was stirred for 1 h at −78° C. and quenched with H$_2$O (30 mL). After the solution warmed to room temperature, it was washed with EtOAc (3×30 mL). The combined organic washes were dried (Na$_2$SO$_4$), filtered and concentrated. The crude keto-ester (0.76 mmol) was dissolved in concentrated acetic acid (4.5 mL) and concentrated HCl (4.5 mL). A reflux condenser was attached and the yellow solution was heated at 120° C. for 16 h. The solution was cooled to room temperature and saturated aqueous K$_2$CO$_3$ was added slowly until pH=6. The suspension was poured into saturated aqueous K$_2$CO$_3$ and washed with EtOAc (3×50 mL). The combined organic washes were dried (Na$_2$SO$_4$), filtered and concentrated. Purification was affected via silica gel column chromatography with 0-5% MeOH/CH$_2$Cl$_2$, then semi preparative reverse phase HPLC. Conditions: 20 mL/min flow rate, gradient of 40-80% CH$_3$CN/H$_2$O over 20 minutes, monitoring at 254 nm. The product eluted at 14.3 minutes. Product fractions were collected and concentrated to remove CH$_3$CN, then washed with EtOAc (3×30 mL). The combined organic washes were dried (Na$_2$SO$_4$), filtered and concentrated. Final purification by silica gel column chromatography with 0-5% MeOH/CH$_2$Cl$_2$ yielded 1-(2,3-Dihydro-benzo[1,4]dioxin-2-yl)-2-(6-methyl-2-p-tolyl-imidazo[1,2-a]pyridin-3-yl)-ethanone (6.0 mg, 2%) as an off-white solid. $^1$H NMR (400 MHz, CDCl$_3$) 7.56-7.50 (m, 3H), 7.42 (s, 1H), 7.23 (d, J=8.07, 2H), 7.04 (dd, J=1.1, 9.2 Hz, 1H), 6.95-6.89 (m, 4H), 4.82-4.80 (m, 1H), 4.51-4.42 (m, 2H), 4.33-4.26 (m, 2H), 2.40 (s, 3H), 2.31 (s, 3H). Mass spectrum (m/e) 399 (M+1)+.

Example 41

From Method C 1-(6-Methyl-2-p-tolyl-imidazo[1,2-a]pyridin-3-yl)-3-thiophen-2-yl-propan-2-one

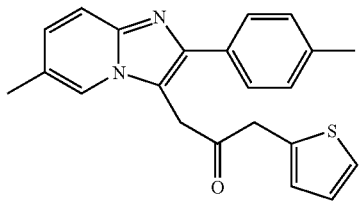

(6-methyl-2-p-tolyl-imidazo[1,2,a]pyridin-3-yl)-acetic acid methyl ester 35a (440 mg, 1.5 mmol) was dissolved in anhydrous THF (15 mL) and cooled to −78° C. Potassium hexamethyldisilazide (0.5M in toluene, 3.0 mL, 1.5 mmol) was added slowly and the resulting bright orange solution was stirred at −78° C. for 10 minutes. Thiophen-2-yl-acetyl chloride (92 µL, 0.75 mmol) dissolved in anhydrous THF (8 mL) was added dropwise to the enolate solution. The resulting yellow solution was stirred for 2 h at −78° C. and quenched with H$_2$O (30 mL). After the solution warmed to room temperature, it was washed with EtOAc (3×30 mL). The combined organic washes were dried (Na$_2$SO$_4$), filtered and concentrated. The crude material was flushed through a pad of silica gel equilibrated with 10% MeOH/CH$_2$Cl$_2$ and concentrated. The crude keto-ester (0.75 mmol) was dissolved in concentrated AcOH (4.5 mL) and concentrated HCl (4.5 mL). A reflux condenser was attached and the yellow solution was heated at 120° C. for 16 h. The solution was cooled to room temperature and saturated aqueous K$_2$CO$_3$ was added slowly until pH=6. The suspension was poured into saturated aqueous K$_2$CO$_3$ and washed with EtOAc (3×50 mL). The combined organic washes were dried (Na$_2$SO$_4$), filtered and concentrated. Purification was affected via silica gel column chromatography with 0-10% MeOH/CH$_2$Cl$_2$, then semi preparative reverse phase HPLC. Conditions: 20 mL/min flow rate, gradient of 40-70% CH₃CN/H₂O over 20 minutes, monitoring at 254 nm. Product eluted at 13.3 minutes. Product fractions were collected and concentrated to remove CH₃CN, then washed with EtOAc (3×30 mL). The combined organic washes were dried (Na₂SO₄), filtered and concentrated to give the title compound (13 mg, 5%) as an off-white solid. ¹H NMR (400 MHz, CDCl₃) 7.85 (d, J=9.17 Hz, 1H), 7.63 (s, 1H), 7.55 (d, J=9.17 Hz, 1H), 7.26-7.18 (m, 5H), 6.98-6.94 (m, 2H), 4.26 (s, 2H), 4.06 (s, 2H), 2.32 (s, 6H). Mass spectrum (m/e) 361 (M+1)⁺.

Example 42

From Method B 2-(6-Methyl-2-p-tolyl-imidazo[1,2-a]pyridin-3-yl)-1-thiophen-3-yl-ethanone

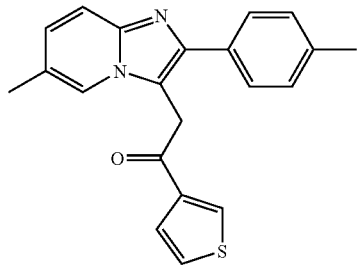

Prepared from (6-methyl-2-p-tolyl-imidazo[1,2-a]pyridine-3-yl)-acetaldehyde 6b and 3-bromo-thiophene using the procedure of Method B described above. ¹H NMR (400 MHz, CDCl₃) δ2.33 (s, 3H), 2.41 (s, 3H), 4.60 (s, 2H), 7.05 (dd, J=1.4 Hz, 9.1 Hz, 1H), 7.30 (m, 4H), 7.53 (d, J=1.4 Hz, 1H), 7.55 (d, J=8.0 Hz, 2H), 7.59 (s, 1H), 7.99 (d, J=1.1, 2.5 Hz, 1H). Mass spectrum (m/e) 347 (M⁺).

Example 43a

From Method B (6-Chloro-8-methyl-2-phenyl-imidazo[1,2-a]pyridin-3-yl)-acetic acid

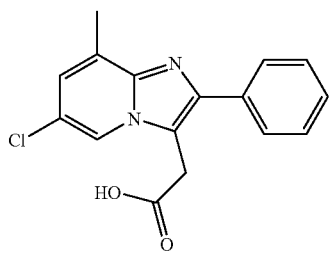

Imidizo[1,2-a]pyridine-3-acetic acid, 6-chloro-8-methyl-2-phenyl-ethyl ester (541 mg, 1.64 mmol) was dissolved in 2:1 TBF:H₂O (15 mL). LiOH—H₂O (134 mg, 3.21 mmol) was added and the slightly yellow solution was stirred for 3.5 h at room temperature. The THF was removed in vacuo and 2 M HCl was added dropwise until pH=6. A white solid slowly came out of solution and was filtered and dried in vacuo overnight to give 291 mg of the title compound.

Example 43b 2-(6-Chloro-8-methyl-2-phenyl-imidazo[1,2-a]pyridin-3-yl)-ethanol

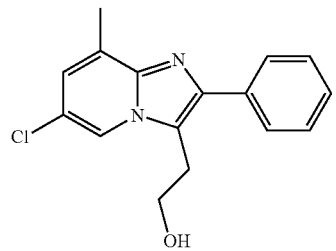

(6-Chloro-8-methyl-2-phenyl-imidazo[1,2-a]pyridin-3-yl)-acetic acid 43a (239 mg, 0.80 mmol) was suspended in anhydrous THF (3 mL) and cooled to 0° C. A borane solution (BH₃.THF) (1.0 M in THF, 2.4 mL, 2.4 mmol) was added, and the resulting opaque solution was stirred at a temperature ranging from about 0° C. to about room temperature over 4 h. All material was in solution after about 1 h. 2 M HCl (5 mL) was added slowly, and the resulting solution was allowed to stir at room temperature for 1 h, then washed with CH₂Cl₂ (3×20 mL). The organic washes were combined and washed with brine (1×20 mL), then dried (Na₂SO₄), filtered and concentrated to give the title compound (209 mg, 92%) as a white solid. ¹H NMR (400 MHz, CDCl₃) δ 8.10 (d, J=1.1 Hz, 1H), 7.55-7.53 (m, 2H), 7.35-7.33 (m, 2H), 6.79 (s, 1H), 3.82 (t, J=5.87 Hz, 2H), 2.99 (at, 2H), 2.49 (s, 3H); ¹³C NMR (100 MHz, CDCl₃) δ 143.1, 142.9, 128.7, 128.5, 127.9, 127.3, 124.8, 120.2, 120.1, 61.8, 27.8, 16.9. Mass spectrum (m/e) 286 (M⁺).

Example 43c (6-Chloro-8-methyl-2-phenyl-imidazo[1,2-a]pyridin-3-yl)-acetaldehyde

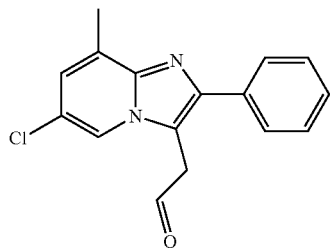

A dry round bottom flask was charged with anhydrous CH₂Cl₂ (4 mL) and anhydrous DMSO (116 μL, 1.63 mmol) and cooled to −78° C. Oxalyl chloride (85 μL, 0.97 mmol) was added and the resulting clear solution was stirred at −78° C. for 1 h. 2-(6-Chloro-8-methyl-2-phenyl-imidazo[1,2-a]pyridin-3-yl)-ethanol 43b (233 mg, 0.81 mmol) was suspended in CH₂Cl₂ (2 mL) and added via syringe to the oxalyl chloride/DMSO mixture. After the resulting yellow/opaque solution had stirred at −78° C. for 1 h, N,N-diisopropylethylamine (Hunigs base) (705 mL, 4.06 mmol) was added. The solution was warmed to 0° C. and stirred for 2 h. Water (20 mL) was added and the crude reaction was washed with CH₂Cl₂ (2×30 mL). The organic washes were combined, dried (Na₂SO₄), filtered and concentrated. The crude product was purified by silica gel column chromatography with 30-80% EtOAc/hexanes to yield the title compound (64 mg, 28%) as an orange oil. ¹H NMR (400 mHz, CDCl₃) δ 9.74 (d, J=1.47 Hz, 1H), 7.77 (s, 1H), 7.63 (d, J=7.70 Hz, 2H), 7.46-7.35 (m, 4H), 7.00 (d, J=0.73 Hz, 1H), 4.09 (s, 2H), 2.63 (s, 3H); DEPT (100 mHz, CDCl₃) CH₃: 17.1, CH₂: 39.6, CH: 196.0, 128.9, 128.8, 128.4, 125.1, 119.0. Mass spectrum (m/e) 285 (M+1)⁺.

Example 43d 2-(6-Chloro-8-methyl-2-phenyl-imidazo[1,2-a]pyridin-3-yl)-1-thiophen-2-yl-ethanol

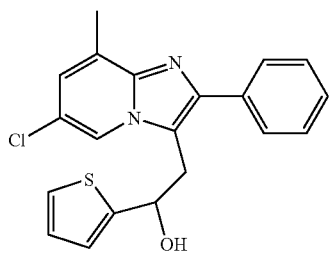

A dry round bottom flask was charged with anhydrous THF (2 mL) and thiophene 2-magnesium bromide solution (1.0 M in THF, 1.3 mL, 1.3 mmol). The solution was cooled to −78° C. and the compound of Example 43c (1917-55) dissolved in anhydrous THF (3 mL) was added dropwise. After 1 h the orange solution was warmed to 0° C. and stirred for 3 h. Water (5 mL) was added and the crude reaction was washed with CH₂Cl₂ (3×20 mL). The organic washes were combined and washed with brine (1×20 mL), then dried (Na₂SO₄), filtered and concentrated. Purification by silica gel column chromatography with 0-40% EtOAc/hexanes gave the title compound (35 mg, 22%) as an orange oil. ¹H NMR (400 mHz, CDCl₃) δ 8.16 (s, 1H), 7.60 (d, J=8.06 Hz, 1H), 7.41-7.35 (m, 3H), 7.27 (d, J=5.13 Hz, 1H), 6.97 (at, 1H), 6.87-6.85 (m, 2H), 5.06 (at, 1H), 3.32 (d, J=6.97 Hz, 2H), 2.54 (s, 3H). Mass spectrum (m/e) 369 (M+1)⁺.

Example 43e 2-(6-Chloro 8-methyl-2-phenyl-imidazo[1,2-a]pyridin-3-yl)-1-thiophen-2-yl-ethanone

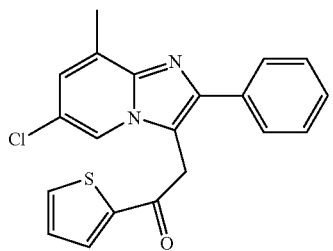

A dry round bottom flask was charged with anhydrous CH₂Cl₂ (2 mL), PCC (22 mg, 0.10 mmol) and sodium acetate/4 Å MS (1:1, 22 mg, 0.10 mmol NaOAc). To the suspension was added 2-(6-chloro-8-methyl-2-phenyl-imidazo[1,2-a]pyridin-3-yl)-1-thiophen-2-yl-ethanol 44d (19 mg, 0.05 mmol) dissolved in CH₂Cl₂ (1 mL). The resulting brown suspension was stirred at room temperature for 5 h. Water (5 mL) was added, and the crude reaction was washed with CH₂Cl₂ (3×20 mL). The organic washes were combined and washed with brine (1×20 mL), then dried (Na₂SO₄), filtered and concentrated. Purification by preparative TLC with 5% MeOH/CH₂Cl₂ gave the title compound (4.0 mg, 21%) as a clear oil. ¹H NMR (400 MHz, CDCl₃) δ 7.69 (s, 1H), 7.70-7.62 (m, 4H), 7.48-7.37 (m, 3H), 7.09 (at, 1H), 7.02 (s, 1H), 4.61 (s, 2H), 2.66 (s, 3H). Mass spectrum (m/e) 367 (M+1)⁺

Method E (for the Synthesis of Lactams)

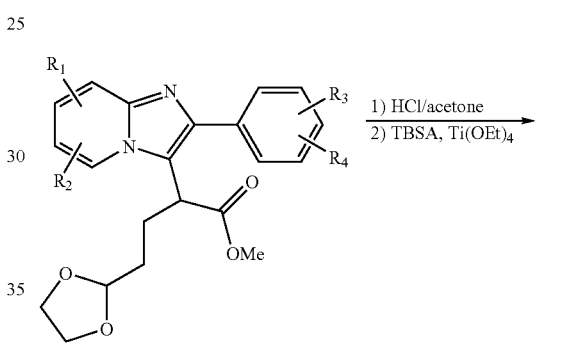

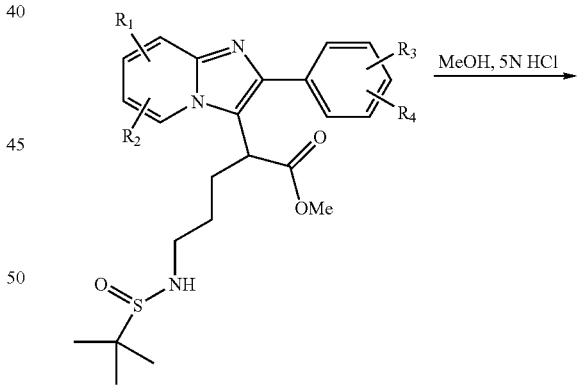

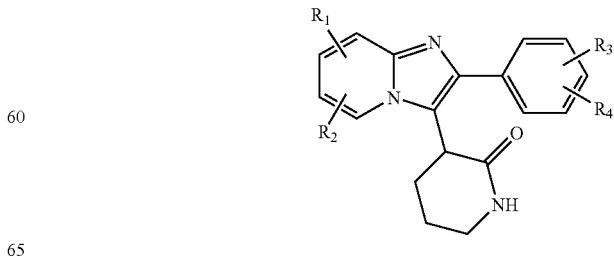

From Method E

Example 44a

From Method E (+/−)-2-(6-Methyl-2-p-tolyl-imidazo[1,2-a]pyridin-3-yl)-5-oxo-pentanoic acid methyl ester

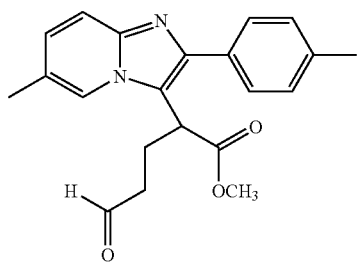

To a magnetically stirred solution of (+/−)-4-[1,3]dioxolan-2-yl-2-(6-methyl-2-p-tolyl-imidazo[1,2-a]pyridin-3-yl)-butyric acid methyl ester 35b (0.10 g, 0.253 mmol) in acetone (5 mL) at room temperature under Ar atmosphere was slowly added 5N HCl (1.5 mL). The reaction mixture was stirred for 2 h and then concentrated in vacuo to remove acetone. NaHCO$_3$ solution (100 mL) was added until the pH is greater than 9, and the aqueous phase was extracted with ethyl acetate (2×100 mL). The combined organic layers were washed with water, dried (MgSO$_4$), and concentrated in vacuo to provide 0.064 g (75%) of the crude product. $^1$H NMR (400 MHz, CDCl$_3$) δ 2.24 (m, 4H), 2.34 (s, 3H), 2.39 (s, 3H), 3.70 (s, 3H), 4.38 (t, J=8.1 Hz, 1H), 7.03 (d, J=1.4 Hz, 1H), 7.24 (d, J=7.3 Hz, 2H), 7.56 (m, 3H), 7.99 (s, 1H), 9.48 (s, 1H).

Example 44b (+/−)-5-(2-Methyl-propane-2-sulfinylamino)-2-(6-methyl-2-p-tolyl-imidazo[1,2-a]pyridin-3-yl)-pentanoic acid methyl ester

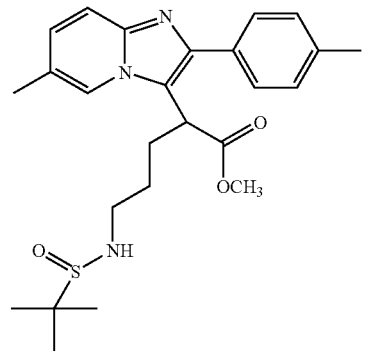

To a magnetically stirred solution of 2-(6-methyl-2-p-tolyl-imidazo[1,2-a]pyridin-3-yl)-5-oxo-pentanoic acid methyl ester 44a (0.066 g, 0.189 mmol) in THF (2 mL) at room temperature under Ar atmosphere was added 2-methyl-propane-2-sulfinic acid amide (0.023 g, 0.189 mmol) and titanium ethoxide (20 wt % solution in ethanol, 2 mL). The reaction mixture was stirred overnight at room temperature. Water (40 mL) was added, and the aqueous phase was extracted with ethyl acetate (2×40 mL). The combined organic layers were washed with water, dried (MgSO$_4$), and concentrated in vacuo. The reaction mixture was redisolved in MeOH (2 mL) and sodium borohydride (0.014 mg, 0.378 mmol) was added at room temperature. The reaction mixture was stirred for 1 h at room temperature, then water (40 mL) was added, and the aqueous phase was extracted with ethyl acetate (2×100 mL). The combined organic layers were washed with water, dried (MgSO$_4$), and concentrated in vacuo to provide crude product.

Example 44c (+/−)-3-(6-Methyl-2-p-tolyl-imidazo[1,2-α]pyridin-3-yl)-piperidin-2-one

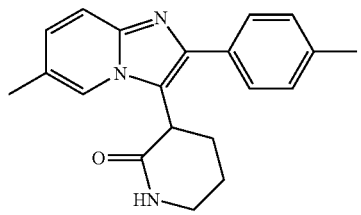

To a magnetically stirred solution of (+/−)-5-(2-methyl-propane-2-sulfinylamino)-2-(6-methyl-2-p-tolyl-imidazo[1,2-a]pyridin-3-yl)-pentanoic acid methyl ester 44b (0.039 g, 0.0824 mmol) in methanol (3 mL) at room temperature under Ar atmosphere was 5N HCl (1.71 mL). The reaction mixture was stirred for 3 h at room temperature, then concentrated in vacuo. The reaction mixture was treated with 10% aq NaOH solution until basic. After 30 min, water (30 mL) was added, and the aqueous phase was extracted with EtOAc (2×50 mL). The combined organic layers were dried (MgSO$_4$), and concentrated in vacuo to the crude product. The pure product was obtained by column chromatography over silica gel (EtOAc, then 4:96 MeOH/EtOAc as eluent) which gave the title compound (0.0202 g, 77%) as a white solid. $^1$H NMR (400 MHz, CDCl$_3$) δ1.92 (m, 1H), 2.04 (m, 2H), 2.16 (m, 1H), 2.32 (s, 3H), 2.39 (s, 3H), 3.50 (m, 2H), 4.28 (dd, J=6.2, 12.4 Hz, 1H), 6.37 (s, 1H), 7.00 (d, J=10.2 Hz, 1H), 7.24 (d, J=8.0 Hz, 2H), 7.56 (m, 3H). Mass spectrum (m/e) 320 (M$^+$).

Method F (for Synthesis of Lactams):

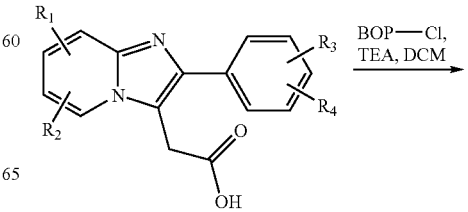

-continued

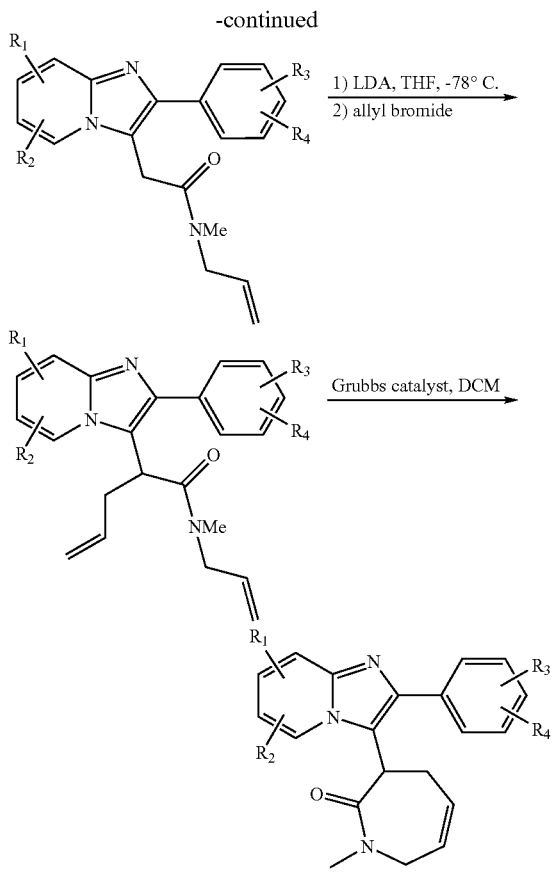

From Method F

Example 45a

N-Allyl-N-methyl-2-(6-methyl-2-p-tolyl-imidazo[1,2-a]pyridin-3-yl)-acetamide

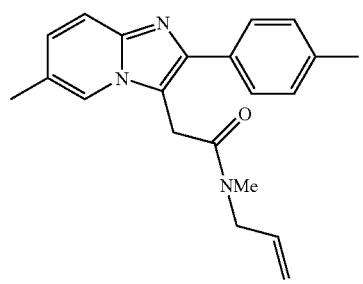

To a magnetically stirred solution of (6-methyl-2-p-tolyl-imidazo[1,2-a]pyridin-3-yl)-acetic acid 1a (1.0 g, 3.57 mmol) at room temperature under Ar atmosphere was added DCM (10 mL), triethyl amine (0.991 mL, 7.14 mmol), bis(2-oxo-3-oxazolidinyl)phosphinic chloride (1.0 g, 3.92 mmol), and allylmethyl amine (0.342 mL, 3.57 mmol). The reaction mixture was stirred overnight at room temperature. Water (40 mL) was added, and the aqueous phase was extracted with DCM (2×40 mL). The combined organic layers were washed with water, dried (MgSO₄), and concentrated in vacuo to produce the crude product. The pure product was obtained by column chromatography over silica gel (20:80 EtOAc/hexanes, then 70:30 EtOAc/hexanes as eluent), which gave the title compound (0.68 g, 60%) as a white solid. ¹H NMR (CDCl₃) δ2.33 (s, 3H), 2.39 (s, 3H), 2.92 (s, 3H), 3.74 (d, J=5.8 Hz, 1H), 3.97 (d, J=5.8 Hz, 1H), 4.08 (d, J=10.6 Hz, 2H), 4.95 (dd, J=1.1, 17.2 Hz, 1H), 5.10 (m, 1H), 5.45 (m, 1H), 7.03 (d, J=9.1 Hz, 1H), 7.25 (m, 2H), 7.53 (m, 3H), 7.99 (s, 1H).

Example 45b (+/−)-2-(6-Methyl-2-p-tolyl-imidazo[1,2-a]pyridin-3-yl)-pent-4-enoic acid allyl-methyl-amide

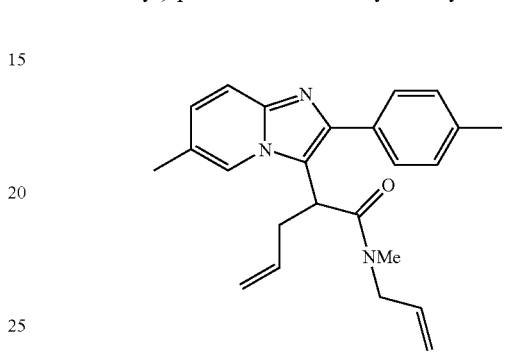

To a magnetically stirred solution of diisopropyl amine (0.35 mL, 2.49 mmol) in THF (10.0 mL) at 0° C. under Ar atmosphere was added n-butyllithium (1.43 mL, 1.6M, 2.29 mmol). The reaction mixture was stirred for 15 min at 0° C., then N-allyl-N-methyl-2-(6-methyl-2-p-tolyl-imidazo[1,2-a]pyridin-3-yl)-acetamide 45a (0.665 g, 2.08 mmol) was added. After an additional 15 min at 0° C., allyl bromide (0.233 mL, 2.70 mmol) was added. The reaction mixture was stirred for 3 h at room temperature. Water (50 mL) was added, and the aqueous phase was extracted with ethyl acetate (2×100 mL). The combined organic layers were washed with water, dried (MgSO₄), and concentrated in vacuo to produce the crude product. The pure product was obtained by column chromatography over silica gel (10:90 EtOAc/hexanes, then 40:60 EtOAc/hexanes as eluent), which gave the title compound (0.24 g, 30%) as a white solid. ¹H NMR (CDCl₃) δ2.31 (s, 3H), 2.37 (s, 3H), 2.73 (m, 1H), 2.77 (s, 3H), 3.25 (m, 2H), 3.84 (m, 1H), 4.40 (m, 1H), 4.50 (m, 1H), 4.80 (m, 1H), 4.95 (d, J=10.2 Hz, 1H), 5.04 (d, J=10.2 Hz, 1H), 5.14 (dd, J=0.7, 17.2 Hz, 1H), 5.82 (m, 1H), 6.99 (m, 1H), 7.23 (d, J=7.3 Hz, 2H), 7.49 (m, 3H), 8.42 (s, 1H).

Example 45c (+/−)-1-Methyl-3-(6-methyl-2-p-tolyl-imidazo[1,2-a]pyridin-3-yl)-1,3,4,7-tetrahydro-azepin-2-one

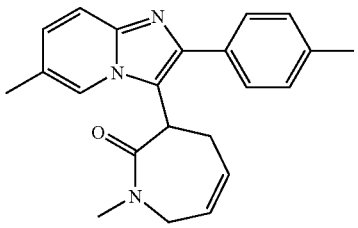

To a magnetically stirred solution of (+/−)-2-(6-Methyl-2-p-tolyl-imidazo[1,2-a]pyridin-3-yl)-pent-4-enoic acid allyl-methyl-amide 45b (0.10 g, 0.268 mmol) in DCM (50 mL) at room temperature under Ar atmosphere was added Grubbs second generation catalyst (1,3-bis-(2,4,6-trimethylphenyl)-

2-imidazolidinylidene)dichloro(phenylmethylene)-tricyclohexylphosphine)ruthenium) (11.5 mg, 0.014 mmol). The reaction mixture was stirred overnight and then concentrated to remove DCM. The pure product was obtained by column chromatography over silica gel (40:60 EtOAc/hexanes, then 90:10 EtOAc/hexanes as eluent), which gave the title compound (0.076 g, 82%) as a white solid. $^1$H NMR (400 MHz, CDCl$_3$) δ2.27 (d, J=2.9 Hz, 1H), 2.32 (s, 3H), 2.39 (s, 3H), 3.11 (s, 3H), 3.29 (m, 1H), 3.45 (dd, J=6.6 Hz, 1H), 4.55 (d, J=12.2 Hz, 1H), 5.09 (dd, J=2.5, 13.5 Hz, 1H), 5.80 (m, 2H), 6.99 (d, J=9.1 Hz, 1H), 7.25 (d, J=7.3 Hz, 2H), 7.48 (m, 3H), 8.20 (s, 1H). Mass spectrum m/e 346 (M$^+$).

As previously stated, the Examples included herein are for illustrative purposes only, and the invention is in no way limited to the embodiments prepared in the Examples.

Activation of GABA receptors leads to alternations in membrane potential (hyperpolarization). The GABA$_A$ receptors are associated with chloride influx through its associated and integrated chloride channel, whereas GABA$_B$ receptor activation indirectly alters potassium and calcium channels as well as modifies second messenger production. The GABA$_A$ recognition sites can be activated by GABA, muscimol, and isoguvacine for example, but not by GABA$_B$ agonists such as baclofen. The modulatory GABA$_A$ recognition site at the benzodiazepine receptor sites can be selectively radiolabeled with 3H-flunitrazepam. The affinity of various potential ligands for the benzodiazepine receptor sites can thus be evaluated by estimating the ability of test compounds to displace $^3$H-flunitrazepam.

Compounds of the invention were assessed for their binding to the benzodiazepine receptor by the test of Speth et al. [*Life Sci.* 24, 351 (1979)] for central benzodiazepine receptors and LeFur et al. [*Life Sci.* 33, 449 (1983)] for peripheral receptors. The compounds were tested first at 1.00E-09, 1.0E-07 and 1.0E-05 M in single determination. In the assays where a compound showed a % inhibition higher than 50% at either concentration, it was tested further at five concentrations in duplicate to obtain competition curves. The specific ligand binding to the receptor is defined as the difference between the total binding and the nonspecific binding determined in the presence of an excess of unlabelled ligand. In each experiment, the respective reference compound was tested concurrently with the test compounds in order to assess the assay suitability. It was tested at several concentrations (for IC$_{50}$ value determination), and the data were compared with historical values. The assay was rendered valid if suitability criteria were met.

For the aforementioned in vitro testing, compounds are defined herein to be active if they have at least 40% inhibition at 10 μM. For in vitro testing, compounds are defined to be inactive if they have less than 40% inhibition at 10 μM. Results of the in vitro testing of representative embodiments of the present invention are shown in Tables 1a, 1b, and 2. However, the invention is not limited to the compounds found in the Tables.

TABLE 1a

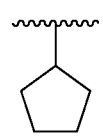

| R$^5$ | IC50 (nM) central | IC50 (nM) peripheral |
|---|---|---|
| —CH$_2$CH(CH$_3$)$_2$ | >10000 | 820 |
| Phenyl | 1750 | 386 |
| —(CH$_2$)$_4$CH$_3$ | 420 | 269 |
| 4-chlorophenyl | 4060 | 594 |
|  | >10000 | 310 |
|  | >10000 | 820 |
|  | 1900 | 560 |
| Methyl | 439 | 231 |
| 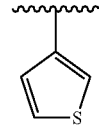 | 38 | 153 |
|  | 1400 | 240 |
|  | 840 | 1600 |
|  | 1300 | 1600 |
|  | 5500 | 3400 |
|  | 2200 | 2000 |

TABLE 1a-continued
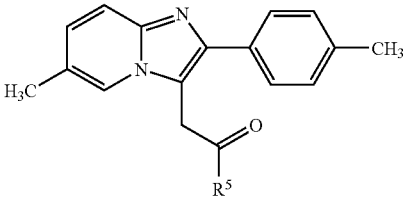
| R⁵ | IC50 (nM) central | IC50 (nM) peripheral |
|---|---|---|
| 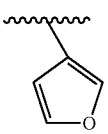 | 590 | 400 |
| 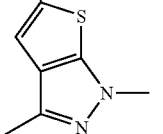 | 180 | >10000 |
| 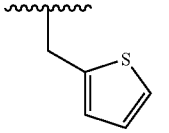 | >10000 | 7600 |
| 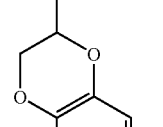 | 2100 | >10000 |
| 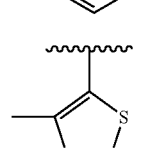 | >10000 | 210 |
| 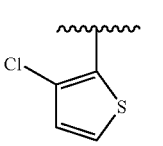 | >10000 | 220 |
TABLE 1a-continued
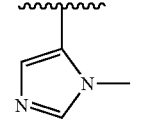
| R⁵ | IC50 (nM) central | IC50 (nM) peripheral |
|---|---|---|
| 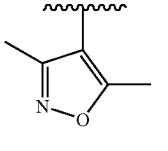 | 720 | 2100 |
| 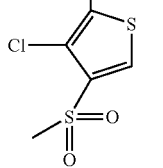 | 1300 | 59 |
|  | 2600 | 32 |
| 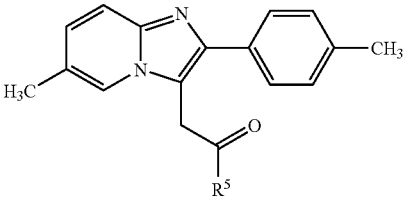 | 2000 | 320 |
| 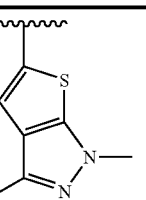 | 950 | 840 |
| 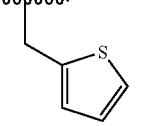 | 40 | 3100 |
| 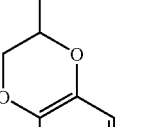 | 650 | 1200 |
| 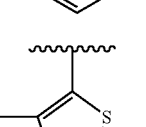 | 200 | 730 |

TABLE 1a-continued
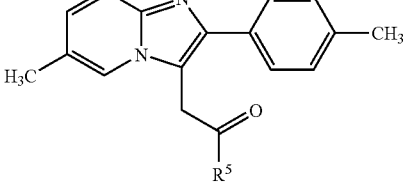
| R⁵ | IC50 (nM) central | IC50 (nM) peripheral |
|---|---|---|
| 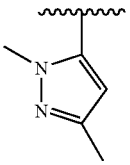 | 91 | 810 |
| 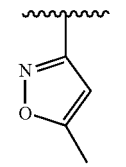 | 1800 | 560 |
| 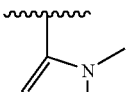 | 84 | >10000 |
|  | 160 | >10000 |
| 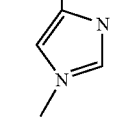 | 1700 | >10000 |
| 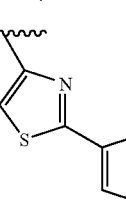 | 110 | 230 |
| 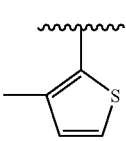 | 1300 | 1700 |
| 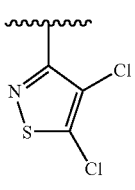 | 750 | 1800 |
TABLE 1a-continued
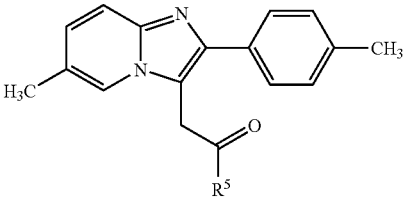
| R⁵ | IC50 (nM) central | IC50 (nM) peripheral |
|---|---|---|
| 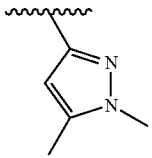 | 360 | 1300 |
| 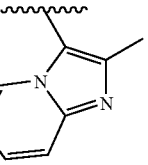 | 16 | 1600 |
| 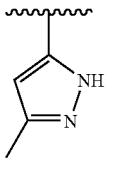 | 6400 | >10000 |
| 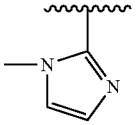 | 3500 | >10000 |
| 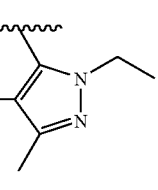 | 2800 | 2100 |
| 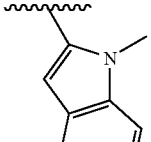 | 1900 | 540 |
| 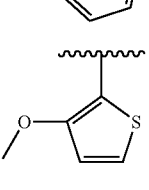 | 36 | 180 |
|  | 100 | >10000 |

TABLE 1a-continued
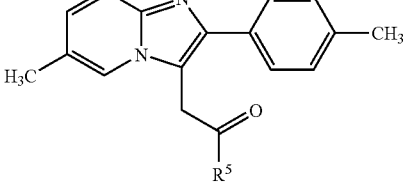
| R⁵ | IC50 (nM) central | IC50 (nM) peripheral |
|---|---|---|
|  | 4800 | 6000 |
| 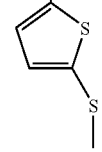 | 33 | >10000 |
| 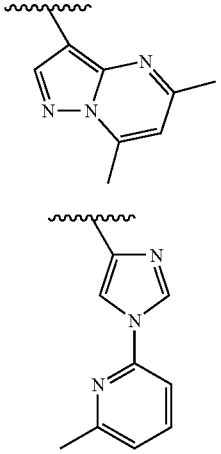 | 2100 | 6600 |
TABLE 1a-continued
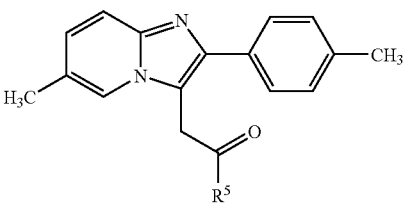
| R⁵ | IC50 (nM) central | IC50 (nM) peripheral |
|---|---|---|
|  | 1100 | 4000 |
| 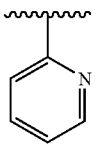 | 650 | 290 |
TABLE 1b
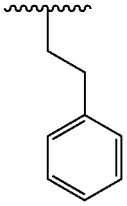
| R⁵ | R¹ | R² | R³ | IC50 (nM) central | IC50 (nM) peripheral |
|---|---|---|---|---|---|
| 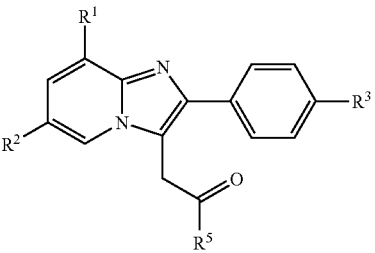 | Methyl | Chloro | Chloro | >10000 | 350 |
| 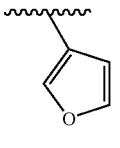 | Methyl | Chloro | Chloro | >10000 | 590 |

TABLE 1b-continued
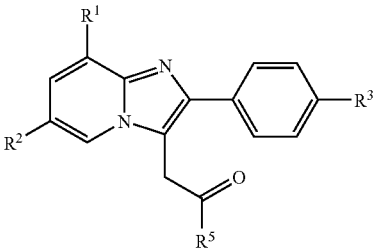
| R⁵ | R¹ | R² | R³ | IC50 (nM) central | IC50 (nM) peripheral |
|---|---|---|---|---|---|
| 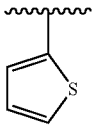 | Hydrogen | Chloro | Hydrogen | 630 | 1200 |
| 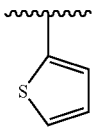 | Hydrogen | Hydrogen | Chloro | 890 | 2600 |
| 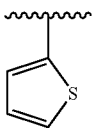 | Methyl | Chloro | Hydrogen | >10000 | 3700 |
| 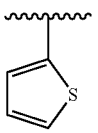 | Hydrogen | Trifluoromethyl | Methyl | >10000 | 650 |
| 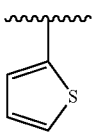 | Hydrogen | Chloro | Chloro | 3600 | 290 |
| 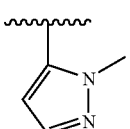 | Hydrogen | Methyl | Methoxy | 8200 | 2300 |
| 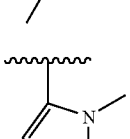 | Hydrogen | Methyl | Methoxy | 420 | 1700 |
|  | Hydrogen | Methyl | Methoxy | 120 | >10000 |

TABLE 1b-continued

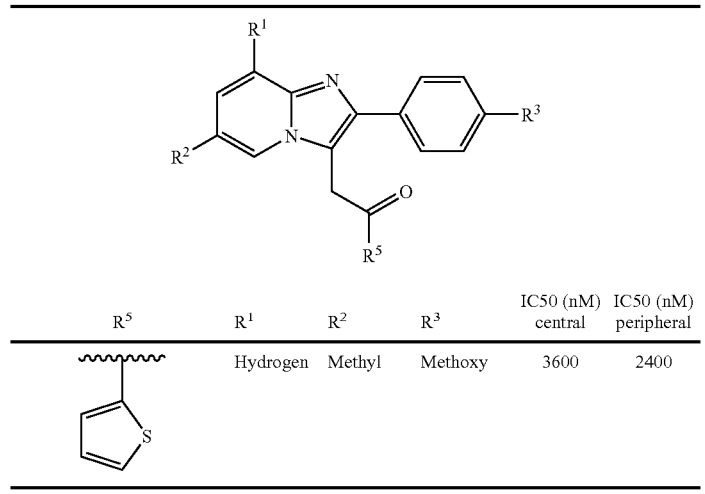

| R⁵ | R¹ | R² | R³ | IC50 (nM) central | IC50 (nM) peripheral |
|---|---|---|---|---|---|
| (2-thienyl) | Hydrogen | Methyl | Methoxy | 3600 | 2400 |

TABLE 2 / TABLE 2-continued

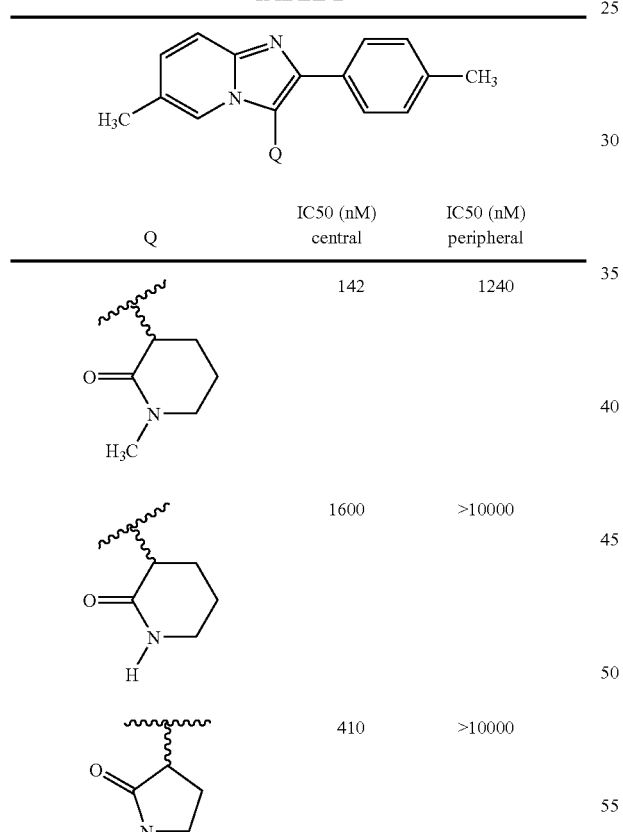
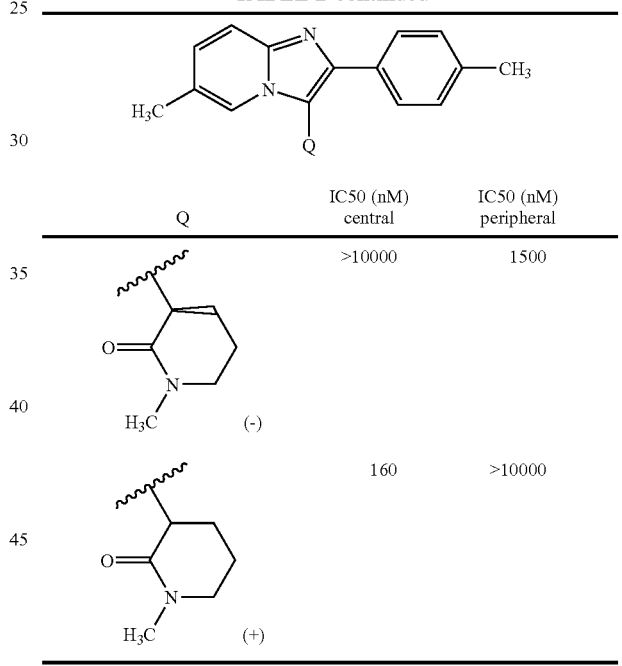

| Q | IC50 (nM) central | IC50 (nM) peripheral |
|---|---|---|
| N-methyl piperidinone | 142 | 1240 |
| NH piperidinone | 1600 | >10000 |
| N-methyl pyrrolidinone | 410 | >10000 |
| N-methyl dihydroazepinone | >10000 | 210 |
| N-methyl piperidinone (−) | >10000 | 1500 |
| N-methyl piperidinone (+) | 160 | >10000 |

The results of these in vitro tests are accepted by persons of skill in the art as predictive of therapeutic utility in vivo.

Preferred embodiments of the current invention have activity versus the benzodiazepine central and/or benzodiazepine peripheral receptor of at least 40% inhibition at 10 μM. More preferably, compounds of the current invention have activity versus the benzodiazepine central and/or benzodiazepine peripheral receptor with an $IC_{50}$ less than or equal to 1 μM. Even more preferably, compounds of the current invention have activity versus the benzodiazepine central and/or benzodiazepine peripheral receptor with an $IC_{50}$ less than or equal to 0.3 μM. Most preferably, compounds of the present invention have activity versus the benzodiazepine central and/or benzodiazepine peripheral receptor with an $IC_{50}$ less than or equal to 0.1 μM.

Furthermore, compounds of the current invention may be two-fold selective for the benzodiazepine central receptor over the benzodiazepine peripheral receptor. More preferably, in this embodiment, compounds of the current invention may be ten-fold selective for the benzodiazepine central receptor over the benzodiazepine peripheral receptor. Even more preferably, in this embodiment, compounds of the current invention may be 50-fold selective for the benzodiazepine central receptor over the benzodiazepine peripheral receptor.

Alternatively, compounds of the present invention may be two-fold selective for the benzodiazepine peripheral receptor over the benzodiazepine central receptor. More preferably, in this embodiment, compounds of the invention may be ten-fold selective for the benzodiazepine peripheral receptor over the benzodiazepine central receptor. Even more preferably, in this embodiment, compounds of the current invention may be 40-fold selective for the benzodiazepine peripheral receptor over the benzodiazepine central receptor.

As another alternative, compounds of the present invention may have similar activity, defined as less than two-fold difference, versus both the benzodiazepine central and peripheral receptors.

Figure 2B:
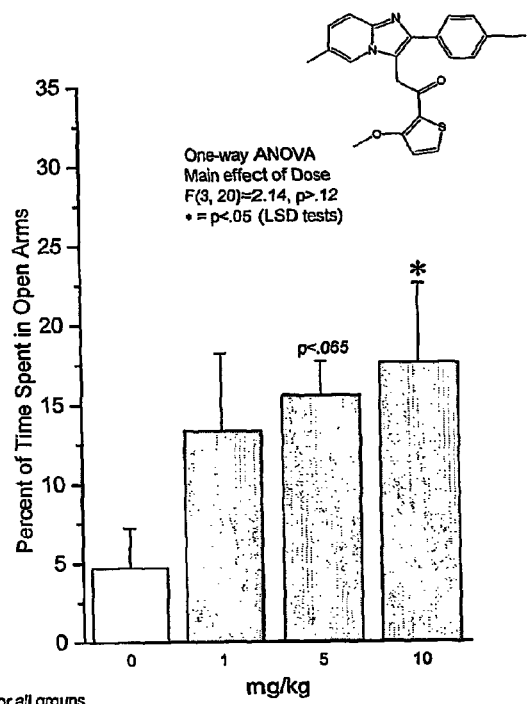
Figure 3A:
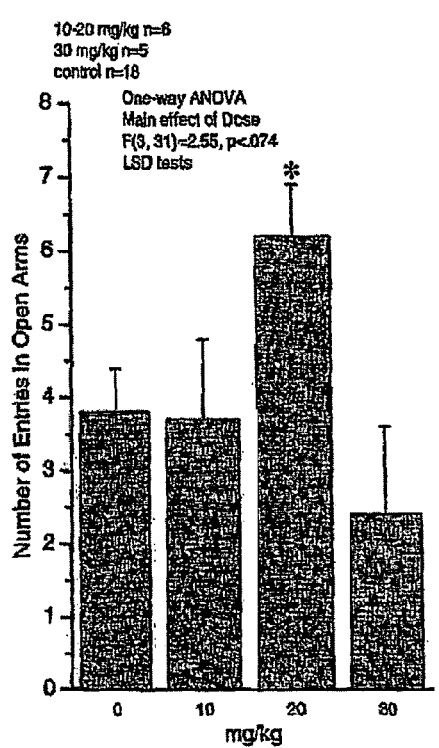
Figure 3B:
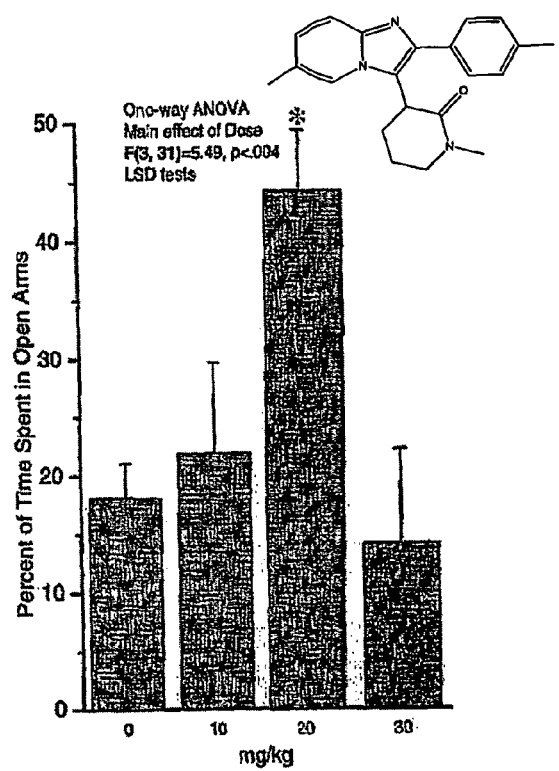

The compounds of Example 1d (also found in Example 6d), Example 22d, and Example 35d, were also tested in vivo using the maze test, which tests anxiety [Montgomery, *J. Comparative and Physiological Psychology* 48, 254-60 (1955); Handley et al., *Naunyn-Schmiedeberg's Archives of Pharmacology* 327, 1-5 (1984); Lister, *Psychopharm.* 92, 180-85 (1987); Pellow et al., *J. Neuroscience Methods* 14, 149-67 (1985); Rodgers et al., *Ethology and Psychopharmacology*, S. J. Cooper and C. A. Hendrie (eds), John Wiley & Sons, Ltd., 9-43 (1994); and Trullas et al., *Psychopharm.* 111, 323-31 (1993)]. The results of the maze test for these compounds are found in FIGS. 1*a*, 1*b*, 2*a*, 2*b*, 3*a*, and 3*b*. FIGS. 1*a*, 2*a*, and 3*a* are graphs of the Number of Entries in Open Arms vs. mg/kg (dose of administered compound). FIGS. 1*b*, 2*b*, and 3*b* plot the Percent of Time Spent in Open Arms vs. mg/kg (dose of administered compound). FIGS. 1*a* and 1*b* indicate that statistically significant activity for the compound of Example 1d (6d) was shown at 10 mg/kg). FIGS. 2*a* and 2*b* indicate that statistically significant activity for the compound of Example 22 was also shown at 10 mg/kg. FIGS. 3*a* and 3*b* indicate that statistically significant activity for the compound of Example 35d was shown at 20 mg/kg. The results of the maze test are accepted by persons of skill in the art as predictive of therapeutic utility.

While it may be possible for the compounds of formulae I and II to be administered as the raw chemical, it is preferable to present them as a pharmaceutical composition. According to a further aspect, the present invention provides a pharmaceutical composition comprising a compound of formula I or formula II, or a pharmaceutically acceptable salt or solvate thereof, together with one or more pharmaceutically carriers and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound of formula I or formula II or a pharmaceutically acceptable salt or solvate thereof ("active ingredient") with the carrier, which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

Formulations for parenteral administration include aqueous and non-aqueous sterile injection solutions, which may contain anti-oxidants, buffers, bacteriostats and solutes which render the formulation isotonic with the blood of the intended recipient. Formulations for parenteral administration also include aqueous and non-aqueous sterile suspensions, which may include suspending agents and thickening agents. The formulations may be presented in unit-dose of multi-dose containers, for example sealed ampoules and vials, and may be stored in a freeze-dried (lyophilized) condition requiring only the addition of a sterile liquid carrier, for example saline, phosphate-buffered saline (PBS) or the like, immediately prior to use. Extemporaneous injection solutions and suspensions may be prepared from sterile powders, granules and tablets of the kind previously described.

Formulations for rectal administration may be presented as a suppository with the usual carriers such, as cocoa butter or polyethylene glycol.

Formulations for topical administration in the mouth, for example buccally or sublingually, include lozenges comprising the active ingredient in a flavoured basis such as sucrose and acacia or tragacanth, and pastilles comprising the active ingredient in a basis such as gelatin and glycerin or sucrose and acacia.

Preferred unit dosage formulations are those containing an effective dose, as hereinbelow recited, or an appropriate fraction thereof, of the active ingredient.

It should be understood that in addition to the ingredients particularly mentioned above, the formulations of this invention may include other agents conventional in the art having regard to the type of formulation in question, for example those suitable for oral administration may include flavoring agents.

The present invention includes compounds of formulae I and II in the form of salts, in particular, acid addition salts. Suitable salts include those formed with both organic and inorganic acids. Such acid addition salts will normally be pharmaceutically acceptable, although salts of non-pharmaceutically acceptable salts may be of utility in the preparation and purification of the compound in question. Thus, preferred salts include those formed from hydrochloric, hydrobromic, sulphuric, citric, tartaric, phosphoric, lactic, pyruvic, acetic, succinic, oxalic, fumaric, maleic, oxaloacetic, methanesulphonic, ethanesulphonic, p-toluenesulphonic, benzenesulphonic and isethionic acids. Salts of the compounds of formula I or formula II can be made by reacting the appropriate compound in the form of the free base with the appropriate acid.

The compounds of the invention may be administered orally or via injection at a dose from 0.001 to 250 mg/kg per day. The dose range for adult humans is generally from 0.5 mg to 10 g/day. Tablets or other forms of presentation provided in discrete units may conveniently contain an amount of compound of the invention which is effective at such dosage or as a multiple of the same, for instance, units containing 5 mg to 500 mg, usually around 10 mg to 200 mg.

The compounds of formula I and II are preferably administered orally. The precise amount of compound administered to a patient will be the responsibility of the attendant physician. However, the dose employed will depend on a number of factors, including the age and sex of the patient, the precise disorder being treated, and its severity. Also, the route of administration may vary depending on the condition and its severity.

All of the patents, patent applications, and other references cited herein are hereby incorporated by reference in their entireties.

Although the foregoing invention has been described in some detail for purposes of illustration, it will be readily apparent to one skilled in the art that changes and modifications may be made without departing from the scope of the invention described herein.

We claim:

1. A compound chosen from formula I and formula II:

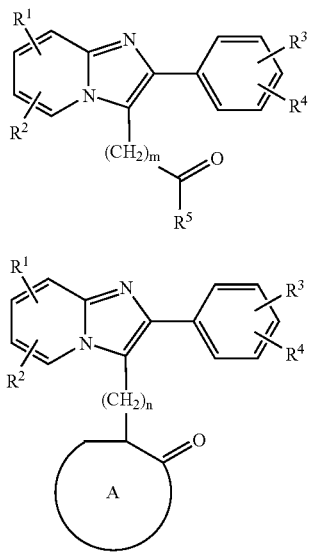

wherein $R^1$, $R^2$, $R^3$ and $R^4$ are chosen independently from the group consisting of hydrogen, halogen, loweralkyl, loweralkoxy, hydroxy, dialkylamino, cyano, acyl, perfluoroloweralkyl, and loweralkylsulfonamido;

$R^5$ is a 7-membered optionally substituted heterocyclyl, with the proviso that if $R^5$ is a nitrogen heterocycle, nitrogen is not at the point of attachment;

A is chosen from an optionally substituted carbocycle, and a 7 or 8-membered optionally substituted heterocycle;

m is one, two or three, with the proviso that, if $R^5$ is methyl, m is not two;

and n is zero, one or two or a salt thereof.

2. A compound according to claim 1 wherein A in formula II is an optionally substituted carbocycle.

3. A compound according to claim 1 wherein A in formula II is a 7 or 8-membered optionally substituted heterocycle.

4. A compound according to claim 3 wherein A in formula II is a seven or eight-membered optionally substituted lactam.

5. A compound according to claim 4 wherein A in formula II is an N-alkyl lactam.

6. A compound according to claim 1 wherein m in formula I is one.

7. A compound according to any of claims 1 or 2 to 5 wherein n in formula II is zero.

8. A compound selected from the group consisting of 1-(2,3-Dihydro-benzo[1,4]dioxin-2-yl)-2-(6-methyl-2-p-tolyl-imidazo[1,2-a]pyridin-3-yl)-ethanone, 1-(2-Methyl-imidazo[1,2-a]pyridin-3-yl)-2-(6-methyl-2-p-tolyl-imidazo[1,2-a]pyridin-3-yl)-ethanone, 1-(5,7-Dimethyl-pyrazolo[1,5-a]pyrimidin-3-yl)-2-(6-methyl-2-p-tolyl-imidazo[1,2-a]pyridin-3-yl)-ethanone, 1-Methyl-3-(6-methyl-2-p-tolyl-imidazo[1,2-a]pyridin-3-yl)-1,3,4,7-tetrahydro-azepin-2-one, 1-Benzo[b]thiophen-2-yl-2-(6-methyl-2-p-tolyl-imidazo[1,2-a]pyridin-3-yl)-ethanone, 1-(5,7-Dimethyl-pyrazolo[1,5-a]pyrimidin-3-yl)-2-[2(4-methoxy-phenyl)-6-methyl-imidazo[1,2-a]pyridin-3-yl]-ethanone, and 1-(2,7-Dimethyl-imidazo[1,2-a]pyridin-3-yl)-2-(6-methyl-2-p-tolyl-imidazo[1,2-a]pyridin-3-yl)-ethanone.

9. A compound selected from the group consisting of 1-(2,3-Dihydro-benzo[1,4]dioxin-2-yl)-2-(6-methyl-2-p-tolyl-imidazo[1,2-a]pyridin-3-yl)-ethanone, 1-(2-Methyl-imidazo[1,2-a]pyridin-3-yl)-2-(6-methyl-2-p-tolyl-imidazo[1,2-a]pyridin-3-yl)-ethanone, and 1-(5,7-Dimethyl-pyrazolo[1,5-a]pyrimidin-3-yl)-2-(6-methyl-2-p-tolyl-imidazo[1,2-a]pyridin-3-yl)-ethanone.

10. A pharmaceutical composition comprising a pharmaceutically acceptable carrier and a compound according to any of claims 1 and 2 to 9.

* * * * *

UNITED STATES PATENT AND TRADEMARK OFFICE
CERTIFICATE OF CORRECTION

PATENT NO. : 7,723,324 B2 Page 1 of 1
APPLICATION NO. : 10/595592
DATED : May 25, 2010
INVENTOR(S) : Fang et al.

It is certified that error appears in the above-identified patent and that said Letters Patent is hereby corrected as shown below:

Title Page, Item (73) Assignee: Delete the "," between "Sepracor and Inc." and insert as --Sepracor Inc.--

Signed and Sealed this

Thirteenth Day of July, 2010

David J. Kappos
*Director of the United States Patent and Trademark Office*